US008005655B2

(12) United States Patent
Baker et al.

(10) Patent No.: US 8,005,655 B2
(45) Date of Patent: Aug. 23, 2011

(54) THERMAL COMFORT MODEL HAVING MULTIPLE FABRIC LAYERS

(75) Inventors: Andrew Thomas Baker, Norcross, GA (US); Linda Connor Sledge, Sandy Springs, GA (US); Kenneth John Zwick, Neenah, WI (US); Ralph Solarski, Alpharetta, GA (US); Audra Wright, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 478 days.

(21) Appl. No.: 12/037,825

(22) Filed: Feb. 26, 2008

(65) Prior Publication Data

US 2009/0216482 A1 Aug. 27, 2009

(51) Int. Cl.
*G06G 7/48* (2006.01)
(52) U.S. Cl. .............................................. 703/6; 374/44
(58) Field of Classification Search ........................ 703/6
See application file for complete search history.

(56) References Cited

U.S. PATENT DOCUMENTS

| 3,688,558 A | 9/1972 | Tixier |
| 4,522,512 A | 6/1985 | Atkins |
| 5,228,779 A | 7/1993 | Kon |
| 5,333,953 A | 8/1994 | Kon |
| 5,749,259 A | 5/1998 | Hamouda et al. |
| 6,331,075 B1 | 12/2001 | Amer et al. |
| 6,408,256 B1 | 6/2002 | Hittle et al. |
| 6,543,657 B2 | 4/2003 | Fan et al. |
| 6,702,456 B2 | 3/2004 | Lu et al. |
| 6,810,300 B1 * | 10/2004 | Woltman et al. .............. 700/132 |
| 6,826,973 B2 | 12/2004 | Puckett et al. |
| 6,918,695 B2 | 7/2005 | Polegato Moretti et al. |
| 6,935,187 B1 | 8/2005 | Gorman et al. |
| 6,991,366 B2 | 1/2006 | Naka et al. |
| 7,037,112 B2 | 5/2006 | Lord et al. |
| 7,099,734 B2 | 8/2006 | Pieper et al. |
| 7,206,728 B2 | 4/2007 | Ozeki et al. |
| 7,216,068 B2 | 5/2007 | Li et al. |
| 7,226,206 B2 | 6/2007 | Romes |
| 2002/0188372 A1 | 12/2002 | Lane et al. |
| 2003/0156619 A1 * | 8/2003 | De Monte et al. .............. 374/44 |
| 2006/0015208 A1 | 1/2006 | Reyes Moreno |
| 2006/0031047 A1 | 2/2006 | Bingham et al. |
| 2007/0173968 A1 | 7/2007 | Koichi |

FOREIGN PATENT DOCUMENTS

JP 6088360 A 5/1985

(Continued)

OTHER PUBLICATIONS

Yi et al, "P-Smart—A Virtual System for Clothing Thermal Functional Design", Computer Aided Design 38, pp. 726-739, Mar. 30, 2006.*

(Continued)

*Primary Examiner* — Mary C Jacob
(74) *Attorney, Agent, or Firm* — Armstrong Teasdale, LLP

(57) ABSTRACT

Modeling a plurality of fabric layers on a subject to predict thermal strain. The computerized model combines subject data, fabric data, and environmental conditions to simulate the thermal comfort of the subject over time. In an embodiment, a user interface enables a user to modify or define the input data to compare the predicted thermal comfort of different garments under the same working conditions.

19 Claims, 18 Drawing Sheets

FOREIGN PATENT DOCUMENTS

JP            6128852 A        2/1986

OTHER PUBLICATIONS

Luo et al, "Education-Oriented Virtual Environment for Clothing Thermal Functional Performance", Computational Science-ICCS, 2007, vol. 4489/2007, pp. 485-492.*

Nelson et al, "Determining Localized Garment Insulation Values from Manikin Studies: Computational Methods and Results", Eur J Appl Physiol, 2005, 95: 464-473.*

Xu et al, "Dynamic Thermal Comfort Numerical Simulation Model on 3D Garment CAD", Applied Mathematics and Computation 182, 2006, pp. 106-118.*

Wang et al, "Computer Simulation of Multi-Phase Coupled Heat and Moisture Transfer in Clothing Assembly with a Phase Change Material in a Cold Environment", Technologies for E-Learning and Digital Entertainment, Lecture Notes in Computer Science, 2006, vol. 3942/2006, 1103-1106.*

Xu et al, "Numerical Solution of a Two-Dimensional Simulation on Heat and Mass Transfer Through Cloth", Applied Mathematics and Computation, 171, 2005, 843-852.*

Zaratuichenko et al, "Human Thermoregulation Model for Space Suit: Mathematical Model for Human Thermal Regulaton in a Suited Mode with Ventilation and Liquid Cooling Capabilities Provided", SAE 972319, 27th International Conference on Environmental Systems, Jul. 14-17, 1997.*

Fiala, D. et al., Computer prediction of human thermoregulatory and temperature responses to a wide range of environmental conditions, Int. J. Biometeorol (2001) 45:143-159.

Jones, B. et al., Heat-moisture interactions and phase change in fibrous material, Thermal and moisture transport in fibrous materials. Ed. N. Pan, P. Gibson, Cambridge, England: Woodhead Publishing Limited, 2004, pp. 425-436.

ISO 7933, International Standard, Ergonomics of the thermal environment—Analytical determination and interpretation of heat stress using calculation of the predicted heat strain, 2004.

Besnard, et al., Predictol®: a computer program to determine the thermophysiological duration limited exposures in various climatic conditions, Computer Methods and Programs in Biomedicine (2004) 76, 221-228.

Blazejczyk, K et al., Radiation Balance in Man in Various Meteorological and Geographical Conditions, Geographia Polonica, 77, 1, 63-76, Spring 2004.

Fanger, P.O., Thermal Comfort, Analysis and Applications in Environmental Engineering, Danish Technical Press, Copenhagen, 1970, pp. 107-133.

PCT International Search Report and Written Opinion of the International Searching Authority mailed on Apr. 30, 2009 regarding PCT/IB2009/050306, 10 pgs.

Rantanen et al., Smart Clothing Prototype for the Arctic Environment, Feb. 2002, ACM, vol. 6, Issue 1, pp. 1-14.

Mori et al., Estimating Human Body Configuration Using Shape Context Matching, 2002, SpringerLink, vol. 2352, pp. 666-680.

* cited by examiner

FIG. 6

$$\frac{2Au(Tu-Tum)}{Rctu} - Am \cdot hcum \cdot (Tum-Tm) - Au \cdot Emu \cdot R \cdot \left[(k+Tmc)^4 - (k+Tum)^4\right] - Au \cdot C1 \cdot Su \cdot \frac{\left[2 \cdot \left(Vu - sp1 \cdot e^{\frac{sp2 \cdot Tum}{sp3+Tum}}\right) hcum \cdot LR \cdot \left(sp1 \cdot e^{\frac{sp2 \cdot Tum}{sp3+Tum}} - Vm\right)\right]}{C1 \cdot Retu} = 0$$

$$Am \cdot hcum \cdot (Tm-Tmc) \frac{2Ac \cdot (Tmc-Tc)}{Rctc} + Au \cdot Emu \cdot R \cdot \left[(k+Tmu)^4 - (k+Tmc)^4\right] - ALum \cdot C1 \cdot \left[\frac{-2 \cdot \left(sp1 \cdot e^{\frac{sp2 \cdot Tmc}{sp3+Tmc}} - Vc\right)}{C1 \cdot Retc} + \frac{hcum \cdot LR \cdot \left(-sp1 \cdot e^{\frac{sp2 \cdot Tmc}{sp3+Tmc}} + Vm\right)}{C1}\right] = 0$$

$$\frac{2Ac(Tc-Tco)}{Rctc} - Ac \cdot hcco \cdot (Tco-Tout) - Ac \cdot Emc \cdot R \cdot \left[(k+Tco)^4 - (k+Trad)^4\right] - ALco \cdot C1 \cdot \frac{\left[2 \cdot \left(Vc - sp1 \cdot e^{\frac{sp2 \cdot Tco}{sp3+Tco}}\right) hcco \cdot LR \cdot \left(sp1 \cdot e^{\frac{sp2 \cdot Tco}{sp3+Tco}} - Vout\right)\right]}{C1 \cdot Retc} = 0$$

$$-Au \cdot Su \cdot \left[ \frac{2 \cdot \left( Vu - sp1 \cdot e^{\frac{sp2 \cdot Tum}{sp3+Tum}} \right)}{C1 \cdot Retu} - \frac{hcum \cdot LR \cdot \left( sp1 \cdot e^{\frac{sp2 \cdot Tum}{sp3+Tum}} - Vm \right)}{C1} \right] + \frac{2 \cdot Au \cdot (Vu - Vum)}{C1 \cdot Retu} - \frac{An \cdot hcum \cdot LR \cdot (Vum - Vm)}{C1} = 0$$

$$-ALmc \cdot \left[ -2 \cdot \frac{\left( sp1 \cdot e^{\frac{sp2 \cdot Tmc}{sp3+Tmc}} - Vc \right)}{C1 \cdot Retc} + \frac{hcum \cdot LR \cdot \left( Vm - sp1 \cdot e^{\frac{sp2 \cdot Tmc}{sp3+Tmc}} \right)}{C1} \right] + \frac{Am \cdot hcum \cdot LR \cdot (Vm - Vmc)}{C1} - \frac{2 \cdot Ac \cdot (Vmc - Vc)}{C1 \cdot Retc} = 0$$

$$-ALco \cdot \left[ \frac{2 \cdot \left( Vc - sp1 \cdot e^{\frac{sp2 \cdot Tco}{sp3+Tco}} \right)}{C1 \cdot Retc} - \frac{hcco \cdot LR \cdot \left( sp1 \cdot e^{\frac{sp2 \cdot Tco}{sp3+Tco}} - Vout \right)}{C1} \right] - \frac{Ac \cdot hcco \cdot LR \cdot (Vco - Vout)}{C1} + \frac{2 \cdot Ac \cdot (Vc - Vco)}{C1 \cdot Retc} = 0$$

THERMAL COMFORT MODEL HAVING MULTIPLE FABRIC LAYERS

BACKGROUND

Thermal strain is a leading cause of discomfort in clothing. Different materials provide different thermal comfort characteristics for a wearer of the materials in a particular environment. Further, changes in material properties result in discernible differences to the wearer. Typically, an actual product use test is required to determine whether a particular change to one of the material properties results in a meaningful difference to the wearer.

Some existing systems attempt to model human thermal comfort. These existing models, however, are limited to a single garment on a human subject or fail to account for various factors such as environmental conditions (e.g., work conditions), garment use scenarios, or physiological data for the specific human subject evaluating the garment. Methods exist that attempt to describe the thermal strain of a human, clothing, environment system. This type of model places emphasis on describing the physiological changes to the subject and characterizes clothing ensembles and fabric layers as a single barrier to heat and moisture movement. This ignores the significance of fabric and air layers as places where heat and moisture may be stored or produced. Other models focus on characterizing heat and moisture movement in fabric layer systems but simplify or ignore the interaction with the subject.

Existing software packages incorporate subject physical properties, their activity level, environmental conditions and clothing characteristics. While these types of models provide insight into thermal stress and thermal comfort for particular clothing ensembles, these existing models do not provide for the calculation of the moisture and thermal insulation properties of these ensembles nor do they account for the dynamics of the fabric properties such as heat of sorption. Additionally they ignore the thermal and moisture capacity of the fabric and air layers and are generally designed only for determining long-term, steady state conditions. Further, the existing models fail to consider the dynamics of the clothing ensemble during usage conditions that are relatively short in duration.

SUMMARY

Embodiments of the invention predict thermal strain by computer modeling a plurality of fabric layers on a subject. At least one gap exists between the layers. Data corresponding to input parameters is received from a user. Output data is generated by the computer model as a function of the received input data. The output data indicates the thermal strain. The user evaluates the fabric layers based on the indicated thermal strain.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 6 illustrates exemplary equations for conservation of energy in an exemplary thermal comfort model.

FIG. 7 illustrates exemplary equations for conservation of mass in an exemplary thermal comfort model.

Corresponding reference characters indicate corresponding parts throughout the drawings.

DETAILED DESCRIPTION

Figure 1:
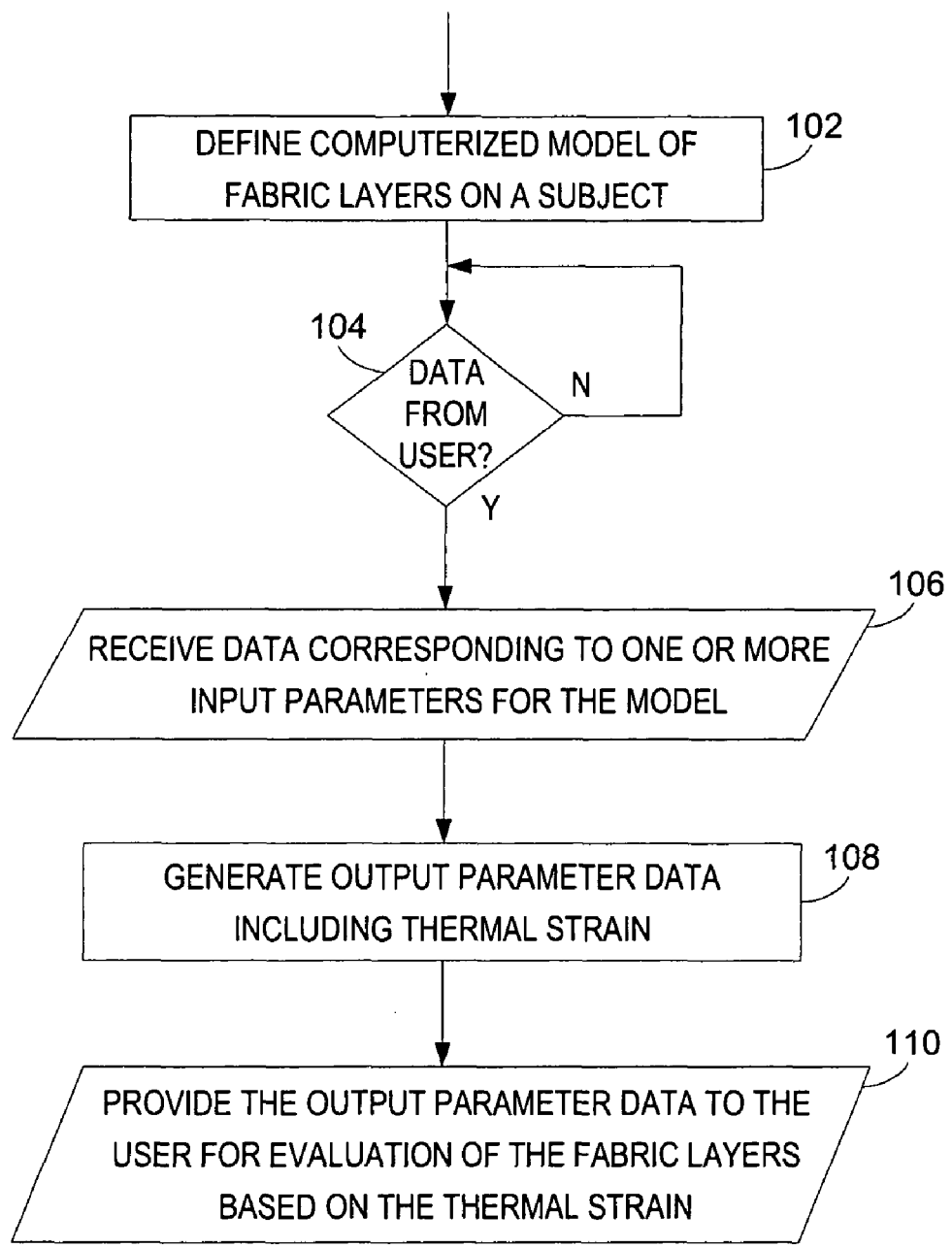
FIG. 1 is an exemplary flow chart illustrating the prediction of thermal strain based on an exemplary thermal comfort model.

Embodiments of the invention predict thermal strain on a subject such as shown in FIG. 1. In an embodiment, the thermal strain is a function of subject data, fabric data, and environmental condition data. The fabric data corresponds to a plurality of fabric layers such as an inner layer and an outer layer separated by a gap. In an embodiment, the thermal strain is represented by a visual representation of the subject with the fabric layers. Other aspects of the invention provide an interactive model enabling users to provide and adjust input data to compare and evaluate fabric layers. Users may provide input data corresponding to particular garments to predict and compare the thermal strain resulting from the garments being worn by the subject. For example, aspects of the invention predict the physiological response by the subject to a particular user activity level, external environment conditions, and clothing layers including protective garments.

It will be appreciated that the exemplary thermal comfort model illustrated and described herein is applicable to any combination of fabric layers on a subject. The fabric layers may be woven materials, knit materials, films, and nonwoven webs including, but not limited to spunbond, meltblown, spunbond/meltblown/spunbond, hydroentangled materials, air laid and wet laid structures. Without undue experimentation, the model is applicable to any fabric, garment, or article of clothing that comes into contact with any portion of the subject. For example, the applicable garments include coveralls, surgical gowns, outdoor apparel, and the like. Further, the subject may be any object that interacts with its environment in the form of heat and moisture. As an example, the subject may be a human or any other animal.

Referring again to FIG. 1, an exemplary flow chart illustrates the prediction of thermal strain based on an exemplary thermal comfort model. The model provides a technical basis for understanding thermal comfort in various fabrics including coveralls, surgical gowns, outdoor apparel, or other garments or articles of clothing. The applicable garments may be disposable, semi-durable, or durable. The prediction of thermal strain estimates the impact of fabric changes without requiring a use test. At 102, a computerized model of a plurality of fabric layers on a subject is defined. The fabric layers have at least one gap between them. The process loops at 104 until data is received from a user. Data is received at 106 from the user. The received data includes, for example, data corresponding to one or more input parameters for the defined model. Alternatively or in addition, the received data may be a command to execute the model based on default inputs, or data relating to one or more characteristics of the subject, garment, or environmental conditions (e.g., work situations). The model executes based on the received data to predict thermal strain. Output parameter data is generated at 108 as a function of the defined model and the received data. The generated output parameter data is provided to the user at 110. The user evaluates the fabric layers based on the output parameter data.

The term 'fabric' refers to woven, knitted, nonwoven, and film materials such as spunbond, meltblown, spunbond/meltblown/spunbond, film laminates, and other like materials. The outer fabric layer may represent for example Coveralls, surgical gowns, etc. These fabric layers can be designed to be disposable, semi-durable, or durable.

For example, aspects of the invention enable the user to compare different combinations of fabric layers for product development. Further, the compared combinations of fabric layers may be used to market one of the combinations over another of the combinations. For example, the user is able to identify differences in fabric performance in a particular work condition represented by the input data and to market the fabric layers based on the identified differences. Another example includes determining optimal work-rest cycles for workers wearing the garments based on the predicted thermal strain to which the workers will be subjected.

In an alternative embodiment, the input parameters are identified to the user (e.g., via an application programming interface) and provided to the user along with the defined model for execution. Further, defined data relating to the subject, garment, or environmental conditions is provided to the user (e.g., in one or more databases or files).

Figure 2:
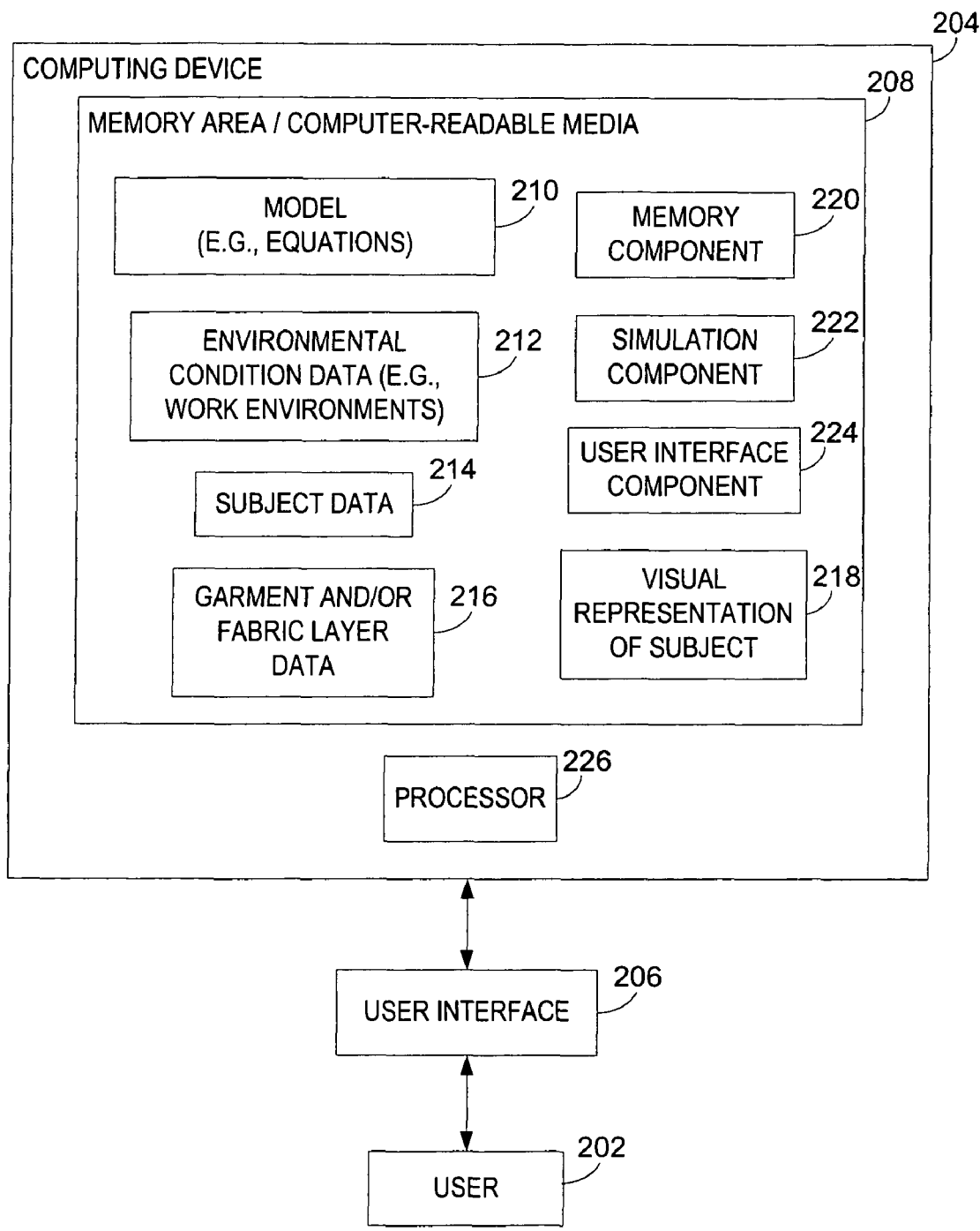
FIG. 2 is an exemplary block diagram illustrating a user interacting with a computing device via a user interface.

Referring next to FIG. 2, an exemplary block diagram illustrates a user 202 interacting with a computing device 204 via a user interface 206. The computing device 204 includes a memory area 208 and a processor 226. The memory area 208 includes one or more computer-readable media. While illustrated as part of the computing device 204, the computer-readable media may be external to the computing device 204 yet connected (e.g., via a network). Further, any combination of the elements illustrated as being stored on the computer-readable media may be stored on separate media.

The memory area 208 stores a computerized model 210 of one or more garments on a subject wherein the garments have at least one gap between them. While the gap is described in examples herein as being an air gap, other gaps such as a liquid gap or a solid barrier between the garments is contemplated. The model 210 includes equations for simulating the garments on the subject, and includes logic for solving the equations in an embodiment. The memory area 208 further stores environmental condition data 212, subject data 214, and garment data 216. The environmental condition data 212 includes, for example, ambient air temperature, humidity, and -ambient air speed. The environmental condition data 212 may also include one or more predefined work environments such as indoor or outdoor construction or a laboratory. In such an embodiment, the processor 226 is configured to receive a selection of one of the predefined work environments and to execute the model 210 based on the selected work environment. In some embodiments, the user 202 is able to modify the predefined work environments or define a new work environment.

The subject data 214 includes, for example, the height, weight, age, gender, metabolic rate, and activity level of the subject. The garment data 216 includes data describing the fabric layers to be modeled on the subject. The garment data 216 includes, for example, fiber type, basis weight, and moisture content, moisture permeability and thermal insulation. Additional examples of the environmental condition data 212, subject data 214, and garment data 216 are listed in Appendix A.

Generally, embodiments of the invention receive data from the user 202 to modify one or more of the environmental condition data 212, subject data 214, and garment data 216 stored in the memory area 208. As an example, at least a portion of the data for the model 210 stored in the memory area 208 is provided to the user 202 for display on the user interface 206. The user 202 selects (e.g., via a user interface selection device), a portion of the displayed model data for modification or provides new model data (e.g., to define a new garment). The model 210 is then executed based on the data received from the user 202.

In general, aspects of the invention are embodied as application programs executing on the computing device 204, applications executing in a networked environment, and/or applications executing as a web service. In the example of FIG. 2, the memory area 208 stores one or more computer-executable components for implementing aspects of the invention. The computer-executable components include a memory component 220, a simulation component 222, and a user interface component 224. The memory component 220 stores the environmental condition data 212, subject data 214, and garment data 216 (e.g., as received from the user 202 or another data source such as a manufacturer of the garment). The simulation component 222 provides the logic for executing the model 210. The user interface component 224 executes in an embodiment of the invention in which the user 202 interacts with the user interface 206.

In operation, the processor 226 is configured to communicate with the memory area 208 and to execute the computer-executable components or instructions. As an example, the user interface component 224 receives input data from the user 202 for the simulation component 222. The input data corresponds to one or more of the data stored by the memory component 220. The simulation component 222 executes based on the input data received by the user interface component 224 to generate output data. The user interface component 224 provides the output data from the simulation component 222 to the user interface 206 for display to the user 202 as an indication of the physiological response by the subject to the input data. In an embodiment, the response by the subject corresponds to the degree of strain on the subject due to the stress (e.g., the stress corresponds to the input data such as the temperature).

In an embodiment, the user interface component 224 provides the output data on a visual representation 218 of the fabric layers or garments on the subject. For example, the visual representation 218 includes a torso of a human subject wearing the garments. Some or all of the output data may be included in the visual representation 218. In some embodiments, the user 202 selects the output data for inclusion in the visual representation 218.

Figure 3:
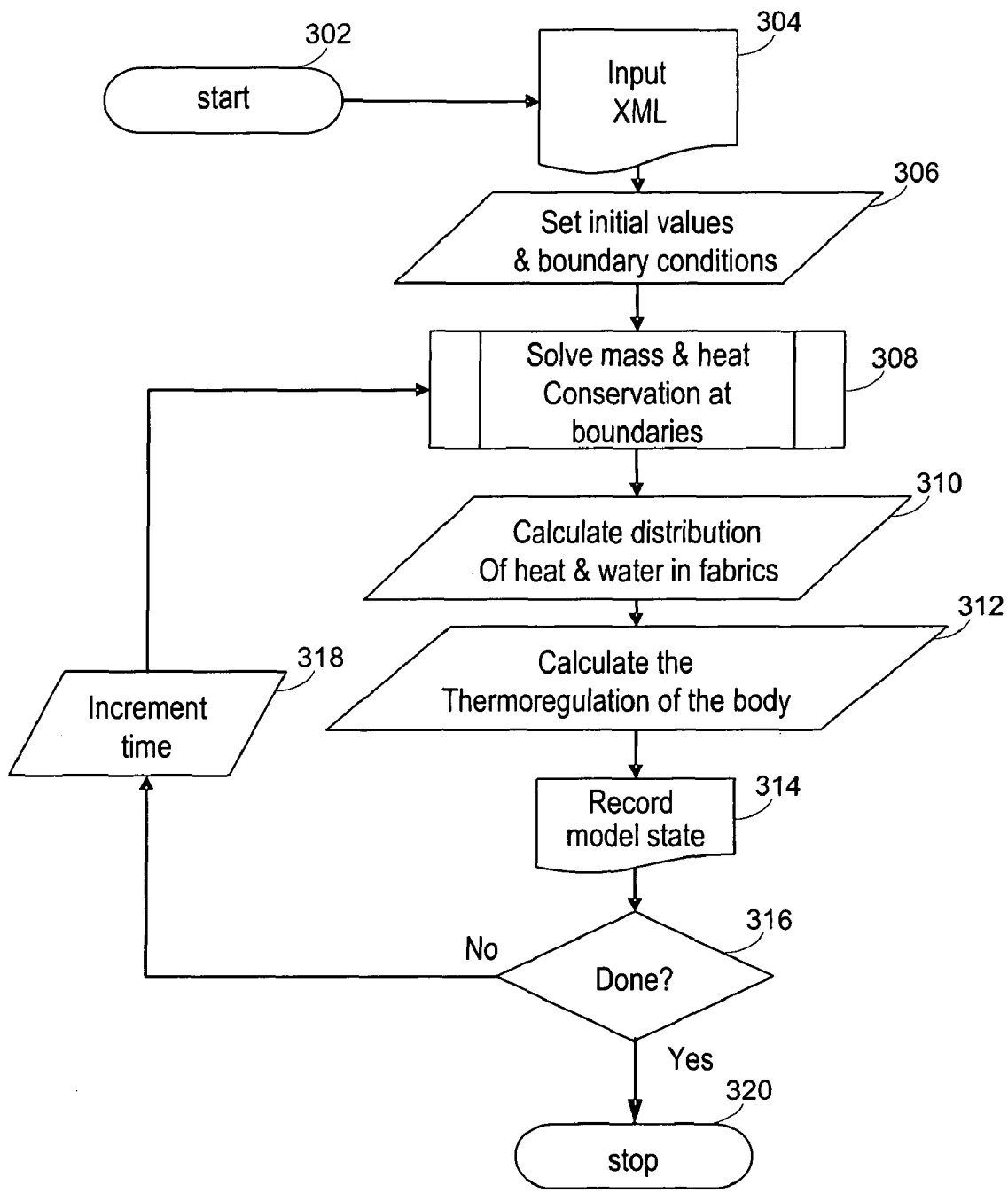
FIG. 3 is an exemplary flow chart illustrating operation of an exemplary thermal comfort model.

Referring next to FIG. 3, an exemplary flow chart illustrates operation of an exemplary thermal comfort model according to an embodiment of the invention. The process begins at 302. At 304, data is input to the model as extensible markup language (XML) data. Initial values and boundary conditions are set for the model at 306. Model equations (e.g., for mass and heat conservation) are solved at 308 based on the set initial values and boundary conditions. The distribution of heat and water in the fabric layers is calculated at 310. The changes in subject physiology due to thermoregulation processes are calculated at 312. The state of the model is stored or recorded at 314. At 316, if the model has completed (e.g., based on the boundary conditions set at 306), the process stops at 320. Otherwise, a time value is incremented at 318 and processing continues at 308.

Figure 4:
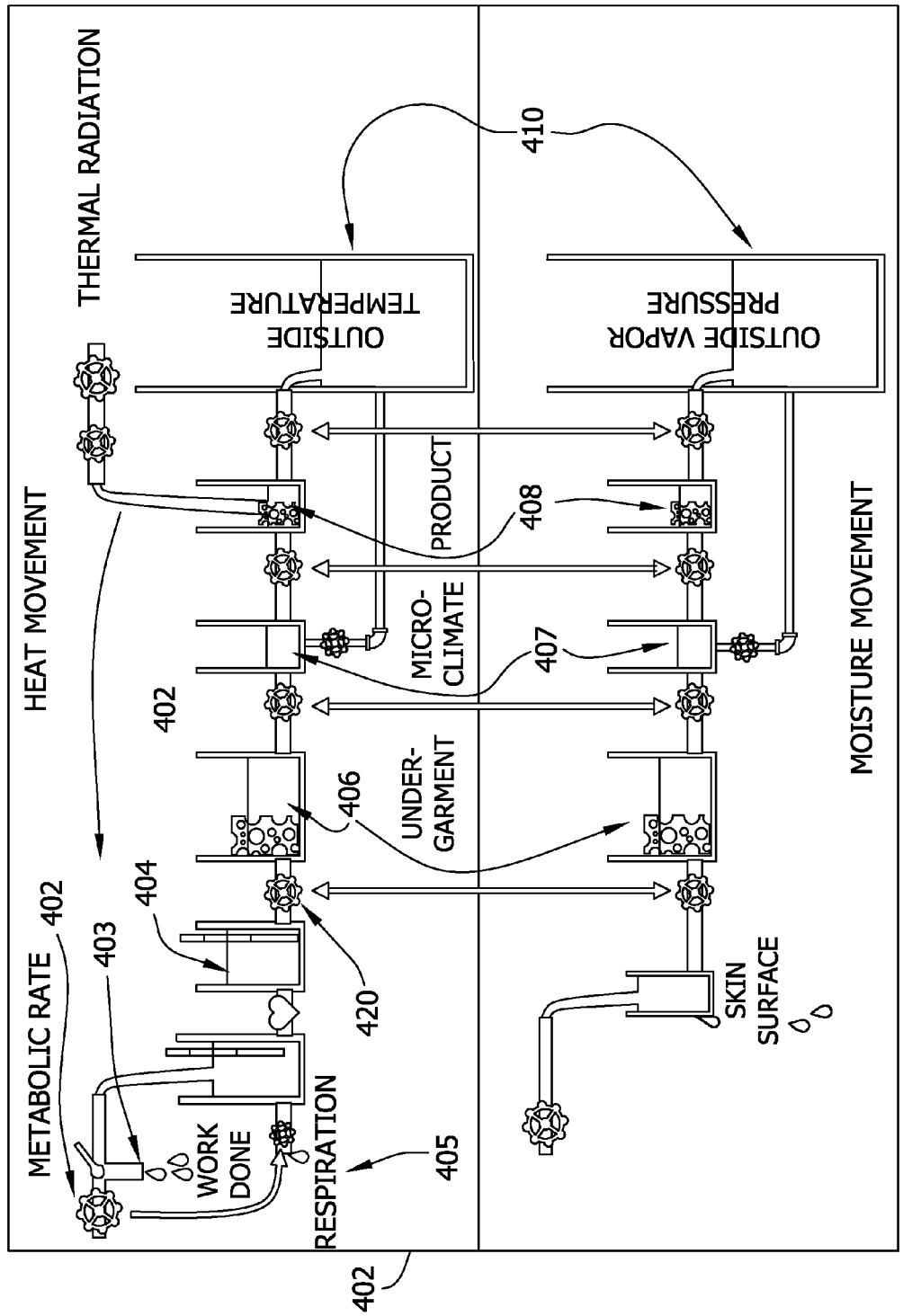
FIG. 4 is an exemplary block diagram illustrating heat and moisture movement in an exemplary thermal comfort model.

Referring next to FIG. 4, an exemplary block diagram illustrates heat and moisture movement 402 in an exemplary thermal comfort model. The exemplary thermal comfort model illustrated in FIG. 4 accounts for thermal regulation. The thermal regulation of the body is due to both the conduction of heat and the evaporation of moisture. The schematic of the moisture movement is nearly identical to heat movement. The chambers represent the locations where heat can accumulate. This includes an inner fabric layer for the undergarments 406 (e.g., t-shirt), an outer fabric layer for the product 408 (e.g., a coverall), and a layer for an air gap between the inner fabric layer and the outer fabric layer (microclimate 407). The rate at which heat transfers from each representative chamber is dependent on the difference in heat (as indicated by water level on the schematic) and how open the valve is between each chamber.

It will be appreciated that the individual layers described and illustrated herein differ from a laminate garment fabric.

The person produces heat in proportion to the work their body is doing. Physical work done 403 by the body is typically at or below 10% of the energy consumed. The large knob on the metabolic rate tube indicates the consumption of energy by the body. The efficiency of the body to convert energy consumed into energy that accomplishes work is represented by the adjacent 'work efficiency' knob. Energy used to do work is removed at this location. The remaining energy is heat energy and fills the body core chamber changing the core temperature.

Heat leaves the body core chamber 404 either through respiration 405 or through loss to the skin layer as heat is transferred by the blood. The rate of loss through respiration depends on the respiration (breaths per minute) and vapor and temperature difference 410 between the lungs and outside air. The rate heat transferred by blood movement depends on the heart rate and the vasodilatation of the capillaries in the skin. Several empirical relationships have been published in the literature that characterize these terms.

The body core chamber has a measuring stick with level markers. If the body temperature rises above the upper mark, the body starts producing sweat as a function of the difference in temperature from the nominal body temperature (33.7° C. for skin, 36.8° C. for body core). Below the lowest mark the body will start shivering to increase metabolic rate. The rate that heat transfers from the skin to the undergarment is dependent on the difference in the two water levels and how open the valve 420 'V1' is. The rate heat increases the temperature in the undergarment chamber (represented by height of fluid) depends on the specific heat of the undergarment fabric (represented by the size of that chamber). Similarly the rate vapor pressure (represented by height of fluid) in the undergarment increases depends on the volume of air in the fabric (represented by size of that chamber). The rate the fluid level rises is dependent on how fast water flows in, and the size of the chamber. The rate temperature increases depends not only on the increase in heat energy, but also the heat capacity of the layer. In the same way heat is transferred to the microclimate from the undergarment. The difference in fluid height (temperature) and the setting of 'V2' knob will drive the rate at which the heat is transferred. And similarly heat into the product 'V3' and heat loss from product into the outside 'V4'. If the garment blocks or slows the transfer of moisture to the outside (as with protective clothing designed to keep dangerous fluids out), the core temperature will continue to rise, and the body will suffer heat stress. The proper design of protective clothing requires taking the flow of heat and moisture through each layer into account.

The 'V1', 'V2', 'V3', and 'V4' knobs determining the rates of heat flux from one chamber to another are related to but not identical to those driving moisture flux from one chamber to another. The "Lewis Relation" for example relates the moisture transfer coefficient to the heat transfer coefficient for the case of air convection driven transfer.

Thermal radiation coming from either sunlight or other sources of radiated heat adds to the product temperature. The large knob indicates the magnitude of the heat source. Direct sunlight for example can average more than 100 W/m$^2$ and can be the predominant heat flux in the system. The small knob on the radiation tube indicates that the heat rate from radiation that enters the fabric depends on the fabric. Reflective fabrics for example reduce the absorption of thermal radiation.

Figure 5:
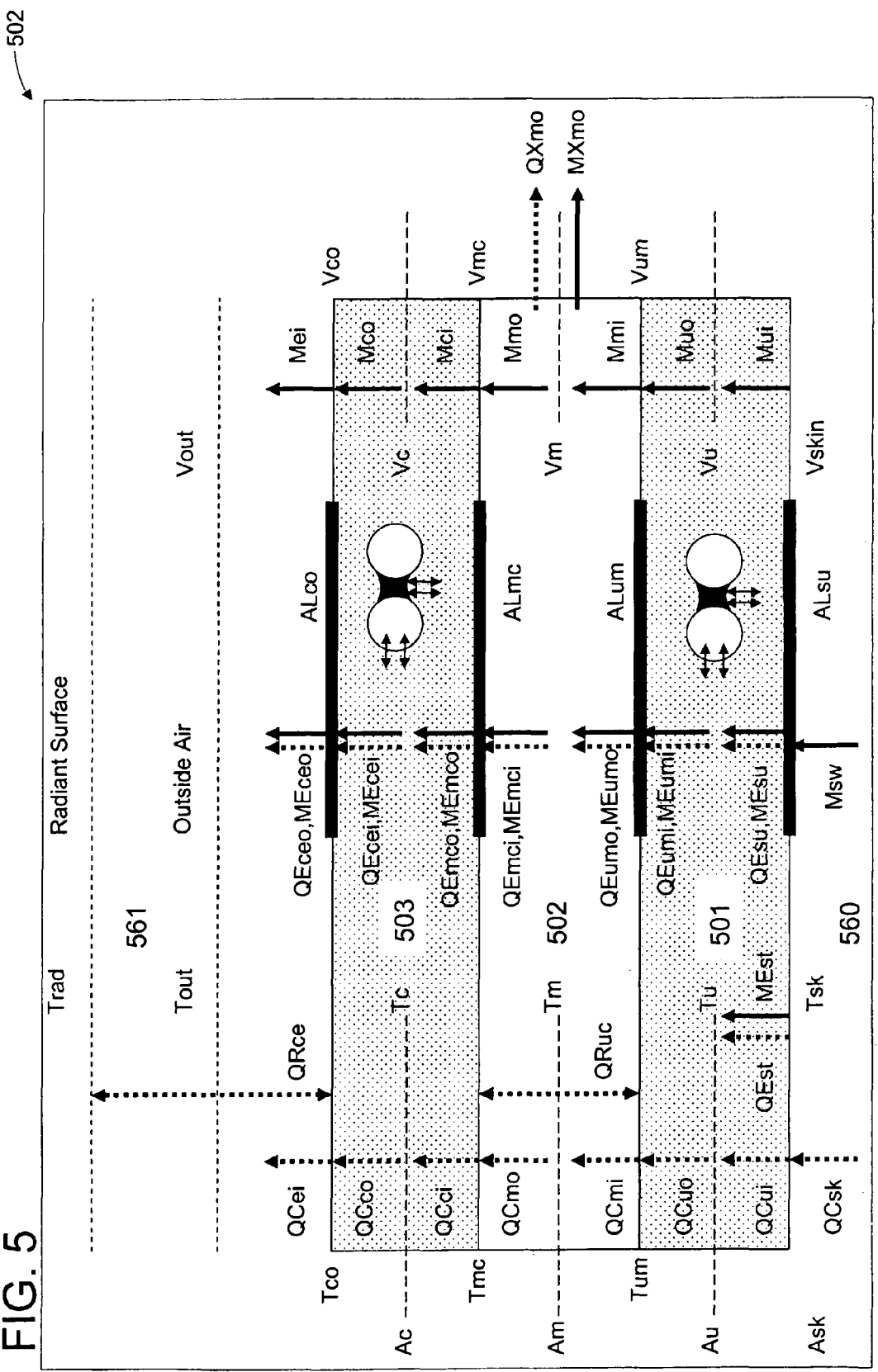
FIG. 5 is an exemplary block diagram illustrating heat and moisture movement among the layers in an exemplary thermal comfort model.

Referring next to FIG. 5, an exemplary block diagram illustrates heat and moisture movement 502 among the layers in an exemplary thermal comfort model. The model is constructed such that at each time step heat energy and water mass are conserved as they move from one layer or portion of one layer to another. Transport mechanisms such as convection, conduction, diffusion, and radiation are considered when calculating the magnitude of the various heat and moisture fluxes. This exemplary model is constructed with one undergarment fabric layer 501 at some average internal temperature of 'Tu' and average internal vapor pressure of 'Vu' adjacent the subjects skin 560 at some average skin temperature of 'Tsk'. Additionally the model has one microclimate air layer 502 at some average air temperature 'Tm' and some average water vapor pressure of 'Vm' between fabric layer 501 and outer garment fabric layer 503. The outer garment fabric layer has an internal temperature of 'Tc' and an internal water vapor pressure of 'Vc'. The outside air layer 561 is adjacent the outer garment fabric layer 503 and is represented by an average air temperature 'Tout' and an average water vapor pressure 'Vout' as well as a radiant surface temperature 'Trad'. The boundary between the undergarment fabric 501 and the microclimate air layer 502 is at some average temperature 'Tum' and average water vapor pressure 'Vum'. The boundary between the microclimate air layer 502 and the outer garment fabric layer 503 is at an average temperature of 'Tmc' and average water vapor pressure of 'Vmc'. Similarly, the boundary between the outer garment fabric layer 503 and the outside air layer 561 has an average temperature of 'Tco', and average water vapor pressure of 'Vco'. The surface area of each of the layers is not necessarily the same and increases as you move outward from the skin. The skin surface area 'Ask' is smaller than the undergarment surface area 'Au'. The microclimate surface area 'Am' is taken to be the average of 'Au' and the outer garment surface area 'Ac'. It should be recognized that the inside surface of one fabric layer does not necessarily have the same surface area as the outside surface of the same fabric layer. In the case of some thick outer garments the difference is meaningful and should be incorporated into the model. The heat and moisture fluxes into the fabric and air layers in the model are not necessarily the same as the fluxes out of these layers. The difference between the fluxes going in and coming out is accumulation or depletion of moisture and or heat in that layer. Any such accumulation or depletion of heat and moisture change the temperature and moisture content of that layer respectively. The arrows represent heat and moisture fluxes at a particular point in time. The terms starting with QC represent heat fluxes due to convection. Terms starting with M are moisture fluxes due to convection. Terms starting with QR represent heat fluxes caused by thermal radiation. Terms starting with QE are heat fluxes from either evaporation or condensation of liquid. The ME terms represent moisture fluxes caused by evaporation or condensation. A detailed description of these terms is provided in Appendix C.

The term 'MEst' represents moisture lost through the skin from diffusion. This transepidermal water loss (TEWL) is proportional to the gradient of moisture in the stratum corneum layer. The moisture content of the outside surface of the skin depends on the relative humidity of the air in contact with the skin. The relative humidity of the air is further dependent on the temperature and vapor pressure of that air which is in turn dependent on the transepidermal water loss. It is possible to include the calculations for transepidermal water loss as part of the thermal comfort model. A natural consequence of the calculation of TEWL is an estimate of the moisture content of the stratum corneum. Various physical properties of the skin, for example permeability to chemicals, can therefore be estimated.

Figure 5A:
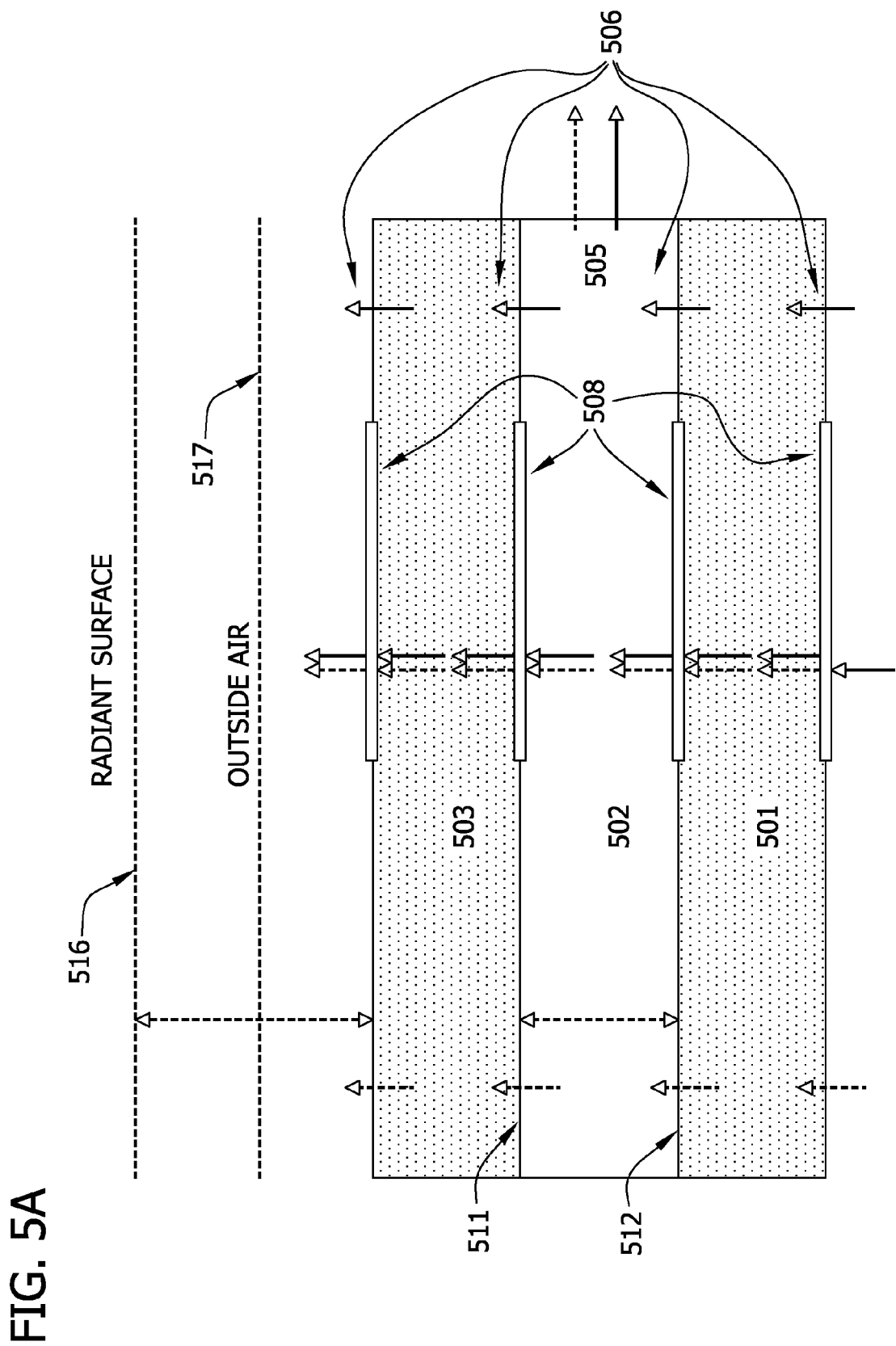
FIG. 5A is an exemplary block diagram illustrating heat and moisture movement among the layers in an exemplary thermal comfort model.

Referring to FIG. 5A, an exemplary block diagram illustrates heat and moisture movement among the layers in an exemplary thermal comfort model. The boundary 512 between the fabric layer 501 and the air gap layer 502 has convective heat transfer from the fabric 501 into the adjacent air 502. Heat transfer from radiation at boundary 512 leaves fabric 501 and enters fabric 503 at boundary 511. Radiation of heat from the outside fabric layer 503 is exchanged with an outside radiant surface 516 that is not necessarily at the same temperature as the surrounding air layer 517. Heat can also be lost or gained by evaporation or condensation of water at boundaries between fabric and air layers. Fluid layers 508 at these boundaries can increase or decrease in size as water is added or removed. Liquid water in these fluid layers 508 can also move by capillary forces in the adjacent fabric layers. The capillary forces are dependent on the contact angle between the liquid and fiber surfaces and is therefore dependent on the material making up the fiber as well as any surface treatments. In an exemplary thermal comfort model any fluid layer 508 at a fabric air boundary is assumed to be absorbed into the fabric when the fiber making up that fabric layer is hydrophilic. Alternate thermal comfort models make use of models of fluid flow in porous structures to calculate the dynamic motion of fluid in the fabric layers. Additionally, transfer of moisture vapor from one layer to another can occur by convection.

Layers of air captured between fabric layers or between fabric and skin are typically in motion due either to natural convection or from forced convection due to bulk air movement. In an embodiment of this invention, the model optionally includes air exchange between the air layer 502 and the outside air 517. This exchange of air 505 can bring in or remove heat and or moisture. Such exchange occurs as air escapes from the microclimate spaces through gaps in the clothing such as those that occur at the cuffs and collar, in such cases air moves around the fabric and not through the fabric. Air exchange through the garment may also be incorporated.

Radiant heat exchange between inner garments 501 and outer garments 503 has been found to be as much as 25% of the overall heat loss from the body. Radiant heat from sunlight can be well over 100 watts per square meter or more in direct sunlight. Radiant heat exchange with the outside environment can be a dominant factor in determining the thermal stress to which the subject is exposed.

The heat and moisture fluxes are balanced in such a way that both heat and moisture are conserved throughout the entire system at any point in time. Any appropriate mathematical procedure may be employed to solve the conservation equations such as the Newton-Raphson method.

Figure 5B:
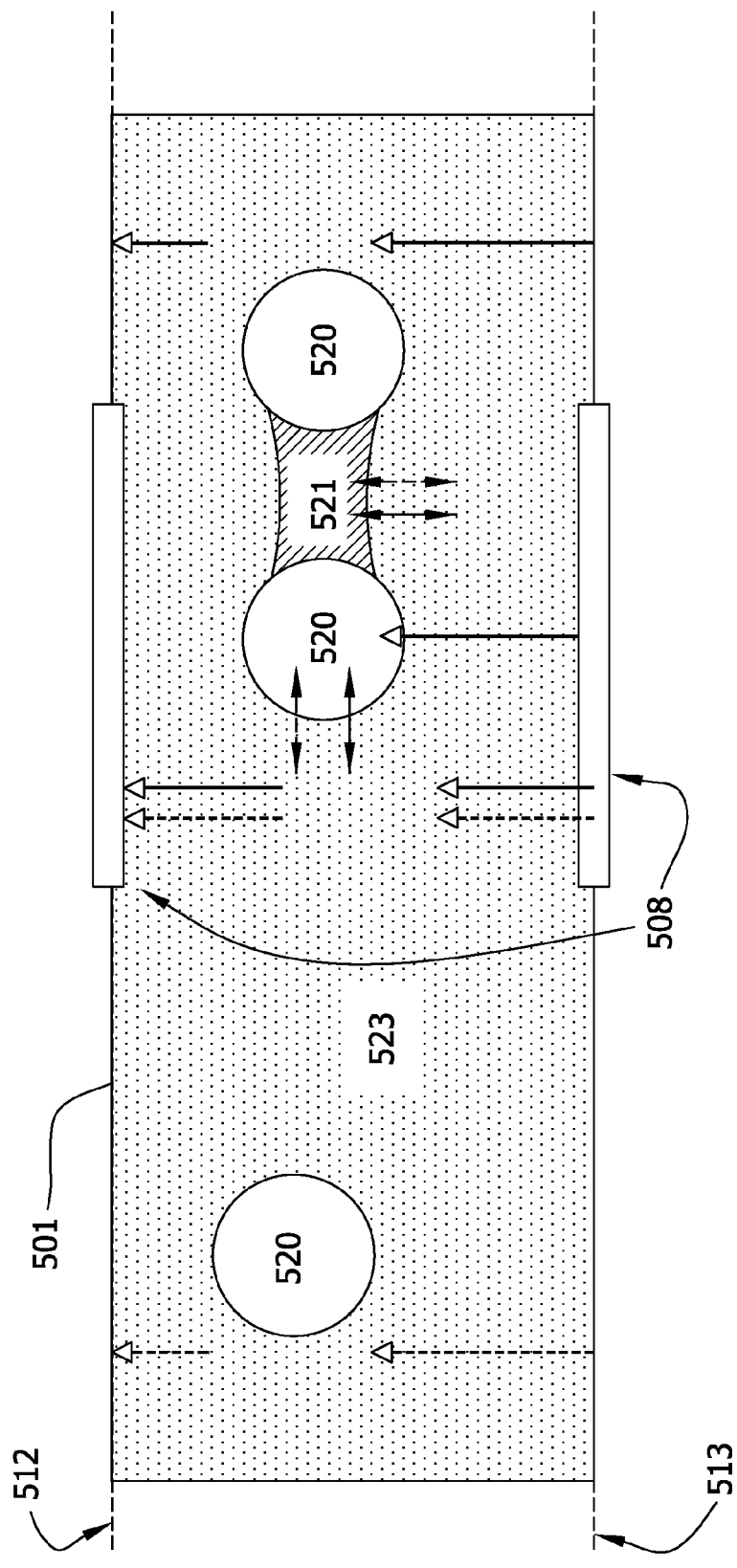
FIG. 5B is an exemplary diagram illustrating heat and moisture transfer within a fabric layer.

Referring to FIG. 5B, an exemplary diagram illustrates heat and moisture transfer within a fabric layer. Heat and moisture transfer into our out of the fabric layer at any point in time will cause redistribution of heat and moisture within the fabric layer. The fabric layer 501 is made up of a mass of fibers 520 and interstitial air 523. In one embodiment of the thermal comfort model changes in heat and moisture are redistributed between fiber, air and liquid water zones such that they are in local equilibrium. In this approach the total fiber 520 moisture content is such that the relative humidity of the air 523 are in equilibrium as determined by sorption isotherm curves representing the specific type of material making up the fiber. The existence of liquid water held in the capillary structure 521 between fibers can occur only when the fibers have reached 100% saturation equivalent to the moisture content on the sorption isotherm curve when the relative humidity is 100%. Liquid at the interfaces 508 will be incorporated into the fabric when the material making up the fibers is hydrophilic. This water is distributed into the fibers 520 as absorbed water and into the interstitial air 523 as humidity. In the case where the air and fibers are saturated or become saturated by incoming water, the additional water is added to water adsorbed onto the fiber surfaces 521. In the case where water is leaving the fabric, the adsorbed water 521 is removed first, and then if needed removed from water absorbed in the fibers and the surrounding air in a proportion determined by the sorption isotherm curve. When water changes state as in the case of absorption into the fiber, or condensation/evaporation from liquid water, heat is generated or absorbed in accordance with latent heat of vaporization or heat of sorption as appropriate.

Referring next to FIG. 6 and FIG. 7, exemplary equations that govern the computational portion of the exemplary thermal comfort model represented in FIGS. 5, 5A, and 5B. FIG. 6 illustrates exemplary equations 602 for conservation of energy while FIG. 7 illustrates exemplary equations 702 for conservation of mass. In an embodiment, the illustrated equations 602, 702 are solved simultaneously based on the input parameter data. Appendix C provides a detailed description of the terms and meaning of each term in the equations.

The accuracy of the exemplary model was confirmed via a comfort study for individuals. The study was designed to cover a range of environmental and use conditions as well as undergarment and outer garment fabrics and styles. The outer garments were disposable protective coveralls with hoods. The coverall fabric did not cover face, hands, or feet. The study conditions were chosen using a Placket-Burman design to maximize orthogonality of the independent variables. Test subjects ingested a temperature probe that provided a continuous measure of core body temperature. Skin temperature was measured in five separate locations. An electrocardiogram was taken throughout the study to indicate heart rate. Chest expansion was measured to quantify breath rate and tidal volume. Sweat loss and evaporation was quantified gravimetrically. Temperature and relative humidity was measured in the air space between the undergarments and coverall. Good correlation was found between the model's predicted values and the results of the comfort study.

Figure 8:
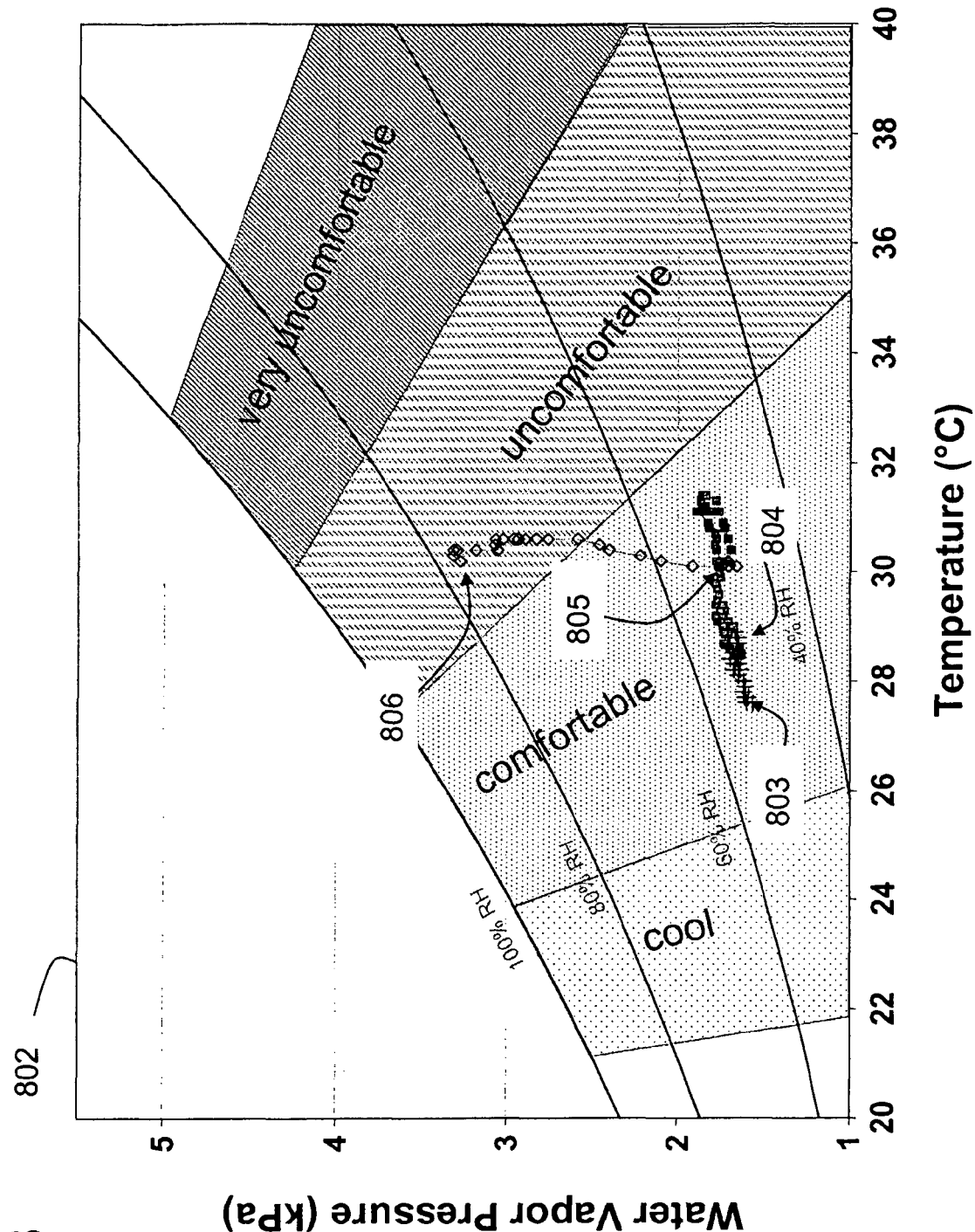
FIG. 8 illustrates exemplary comfort levels in a mapping of water vapor pressure versus temperature.

Referring next to FIG. 8, exemplary comfort levels are illustrated in a graph 802 of water vapor pressure to temperature. The plotted set of points represents the temperature and vapor pressure of the air layer between undergarment and coveralls. The state of the microclimate when the subject dons a coverall is shown at point 803. The subject then acclimates to a new temperature for 30 minutes to point 804. During this time, the temperature increases, but the water vapor pressure stays relatively constant because the subject has not yet begun to sweat to attempt to regulate temperature. The garment is breathable enough to let the sensible perspiration (moisture that transpires through the stratum corneum) pass through. At point 804, the subject begins light stepping exercise for 30 minutes to point 805. Here, the subject begins to sweat to help remove the internal heat generated by the exercise. The water vapor pressure increases, but the temperature stays constant because the air within the garment is not yet saturated and the sweat can evaporate and remove heat at a constant temperature. Even though the temperature remains constant, this subject moves into the uncomfortable range (e.g., point 806) because the increasing humidity makes it more difficult to remove heat efficiently. This figure represents one approach to characterizing thermal comfort of individuals based on the temperature and humidity of the air surrounding a subject's body. Other empirical models exist that provide a PMV or "Predicted Mean Vote" for thermal comfort based on physiological stress indicators like core and skin temperature.

Figure 9:
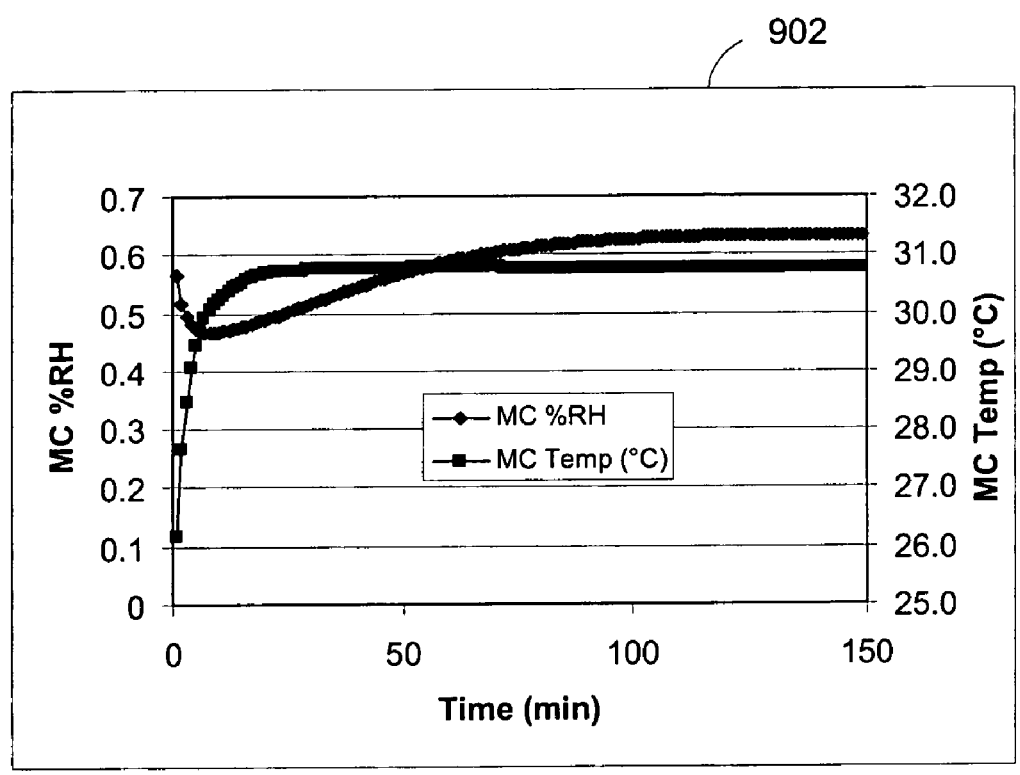
FIG. 9 illustrates sample, calculated temperature and relative humidity values for the air layer between fabrics from an exemplary thermal comfort model.

Referring next to FIG. 9, example output results describing the temperature and percent relative humidity of the air layer between the undergarment fabric and the outer garment are illustrated in a graph 902. This graph illustrates the dynamic nature of the air layer as it accommodates heat and moisture coming and going through the adjacent fabric layers.

Figure 10:
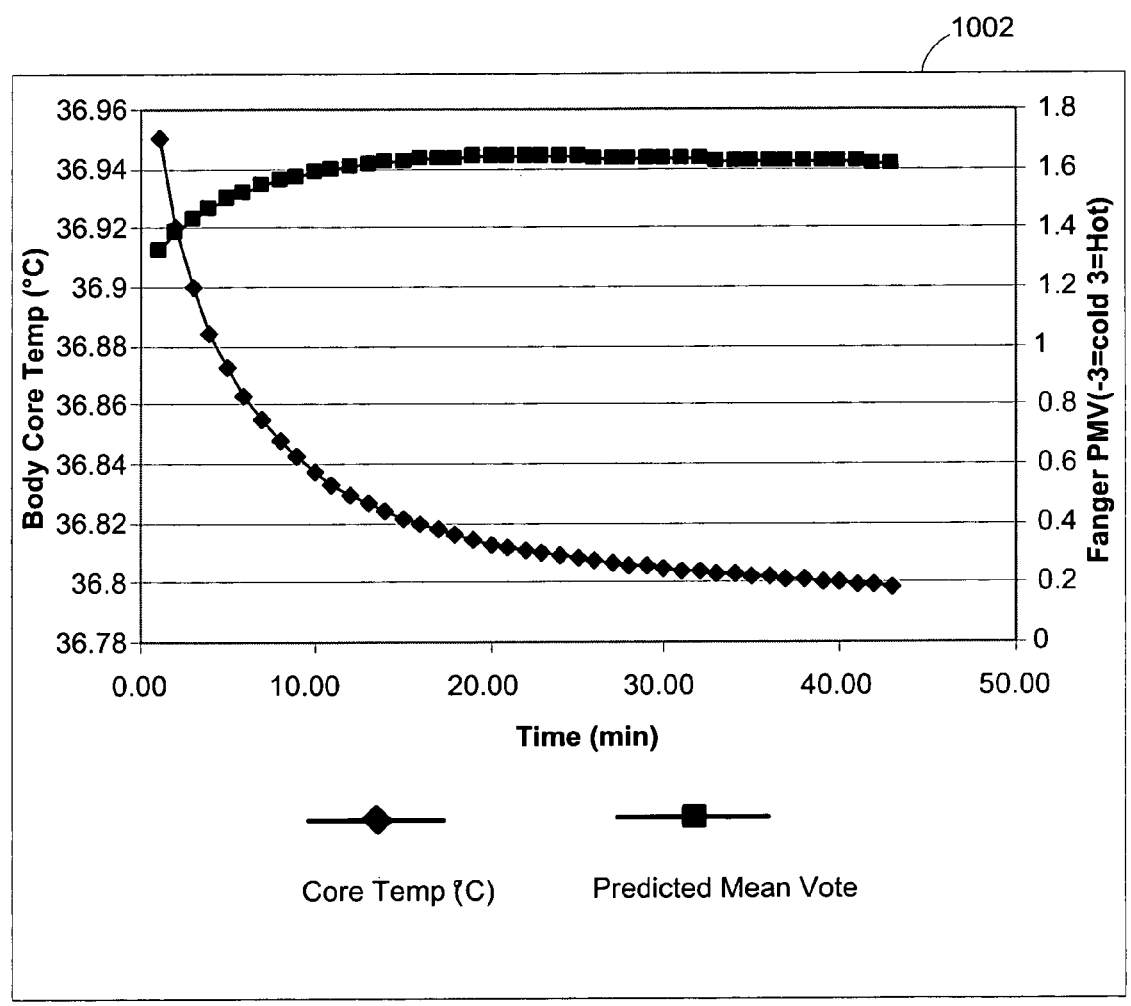
FIG. 10 illustrates sample, calculated body temperature values from an exemplary thermal comfort model.

Referring next to FIG. 10, estimated core body temperature values are graphed as a function of time. In addition, this chart includes the estimated thermal comfort level for this subject. There are many empirical models of thermal comfort, some of which are known in the art. For example, existing literature provides equations relating physiological and environmental state with thermal comfort. This graph 1002 illustrates the change in comfort level as the core body temperature increases over time.

Figure 11:
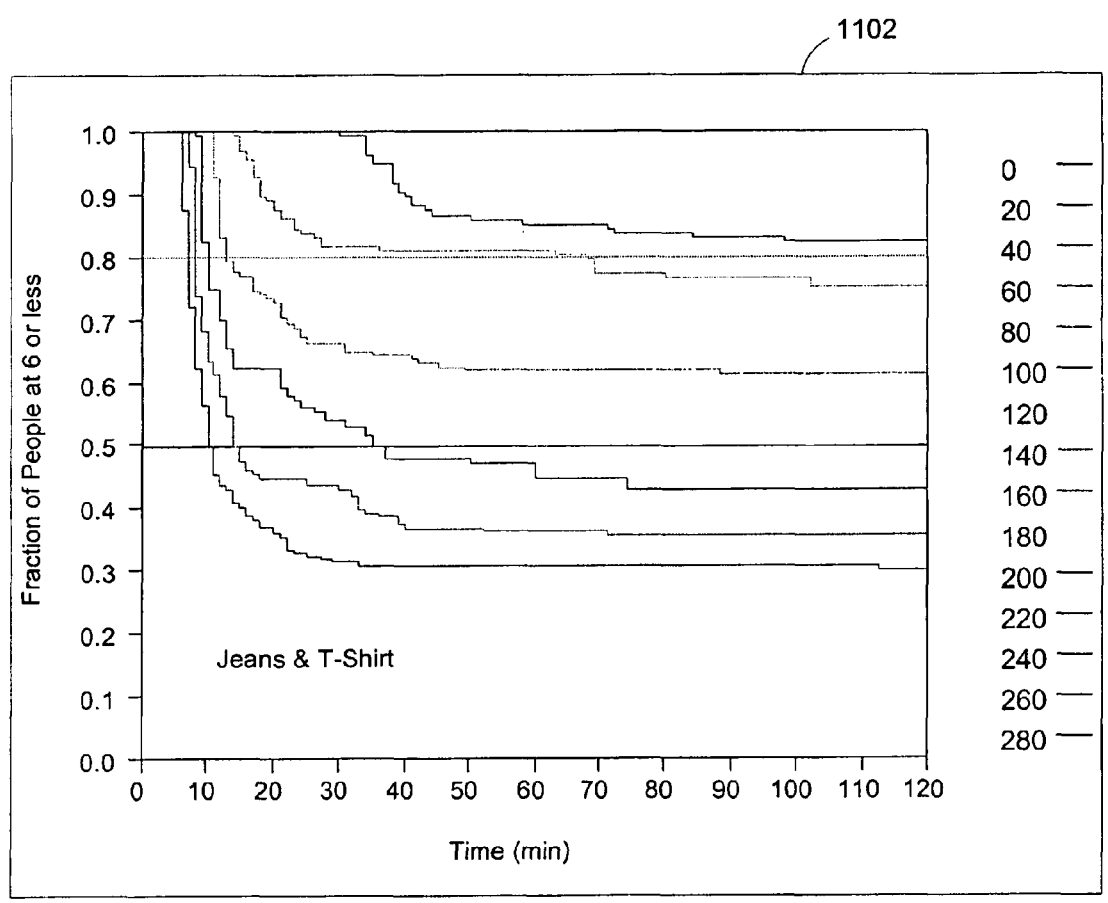
FIG. 11 illustrates a predicted fraction of users wearing a t-shirt and jeans who recorded a particular comfort level as a function of time in a particular environment and at a specified activity level.
Figure 12:
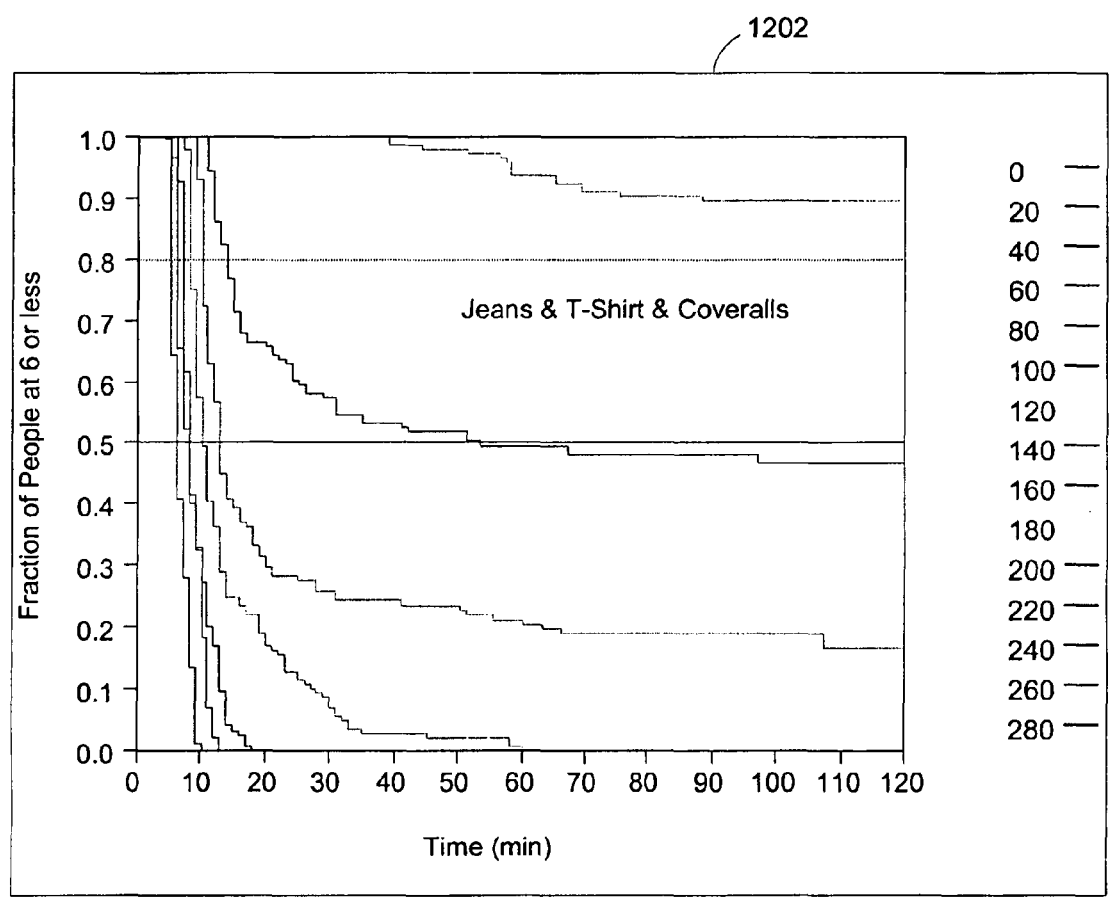
FIG. 12 illustrates a predicted fraction of users wearing a t-shirt, jeans, and coverall who recorded a particular comfort level as a function of time in a particular environment and at a specified activity level.

Referring next to FIG. 11 and FIG. 12, in an embodiment of the thermal comfort model, any of the input parameters to the model are represented not by a single value but by a distribution of values. These graphs serve as examples of the types of comparisons that may be made using the thermal comfort model and distributions of input parameters. The Monte-Carlo type simulation may be employed as a method for estimating any of the output parameters such as thermal strain for a population of input parameters. The graph 1102 provides an example of the predicted fractions of users wearing a t-shirt and jeans who were at a comfort level of six or less on a ten-point scale, with zero being "the coldest you've ever been", five being "neutral, neither cold nor warm", and ten being "the hottest you've ever been". In this graph, the various plotted curves represent different level of cooling applied directly to the skin in watts per square meter. Input parameters for subject weight and height and age were selected randomly from a distribution of subjects.

Referring next to FIG. 12, using the same Monte Carlo method and pulling from the same distribution of subjects, graph 1202 represents the estimated percentage of subjects that were comfortable wearing undergarments and a coverall. When compared with graph 1102 in FIG. 11 it is possible to estimate the percentage increase in uncomfortable subjects when they wear a coverall over T-shirt and Jeans.

Figure 13:
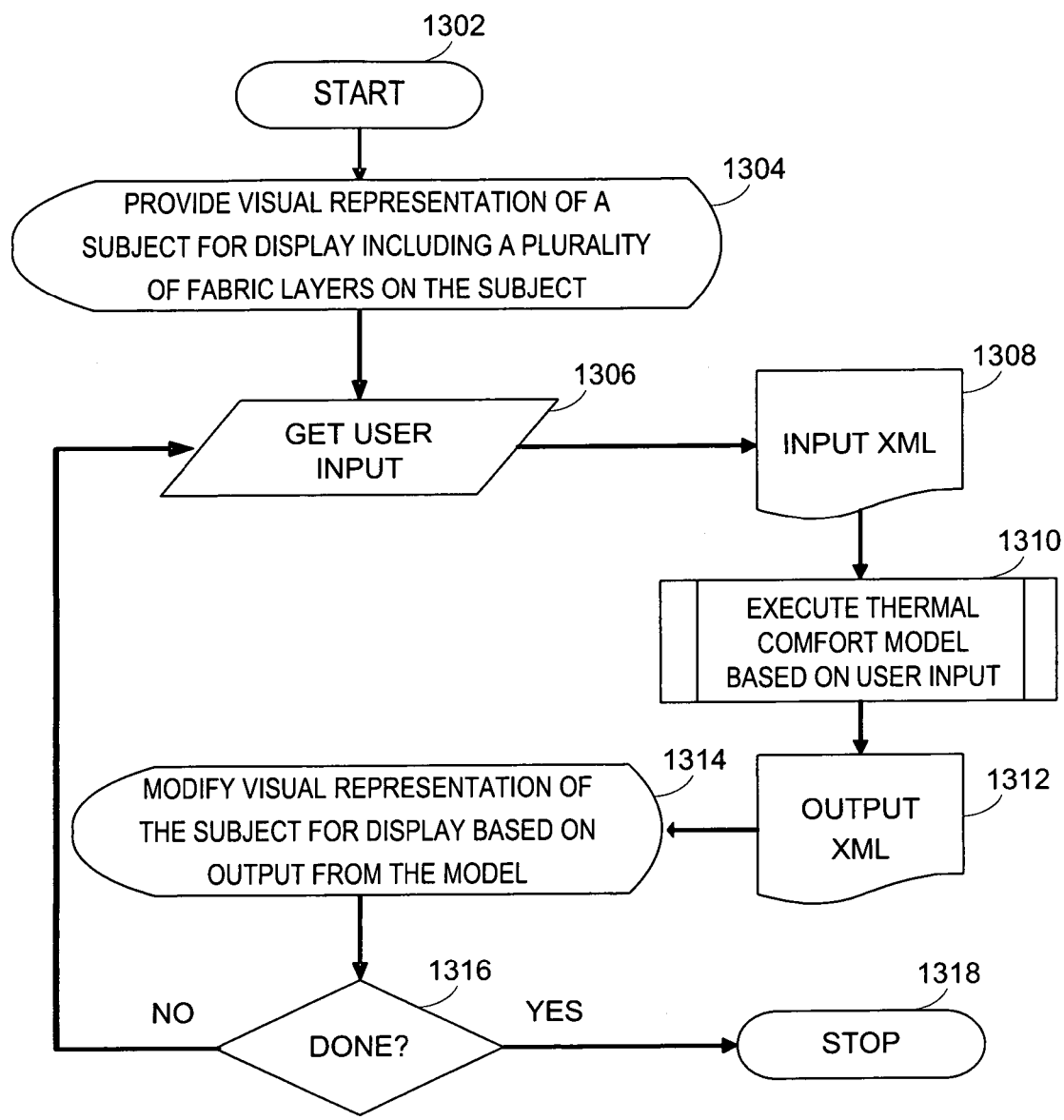
FIG. 13 is an exemplary flow chart illustrating user interaction with an exemplary thermal comfort model.

Referring next to FIG. 13, an exemplary flow chart illustrates user interaction with an exemplary thermal comfort model. The process begins at 1302. At 1304, a visual representation of the subject is provided to a user for display on a user interface. The visual representation includes a plurality of fabric layers on the subject where the fabric layers have at least one gap between them. User input is received at 1306 (e.g., via a user interface selection device such as a pointing device or keyboard) and converted into, for example, XML data at 1308. The thermal comfort model corresponding to the provided visual representation is accessed and executed at 1310 based on the XML data. The model simulates the thermal comfort of the subject wearing the plurality of fabric layers and generates output XML data at 1312. For example, the output XML data indicates a core temperature and hydration level of the subject over a user-defined time period. The hydration may be used as an indication of the skin health of the subject. Alternatively or in addition, the output XML data indicates the permeability of the subject's skin to polar materials and/or non-polar materials such as toxins.

The visual representation of the subject is modified at 1314 based on the generated output XML data to indicate the thermal comfort of the subject. For example, the visual representation of the subject is modified to reflect the core temperature and hydration level of the subject over the user-defined time period. In embodiments, data corresponding to the modified visual representation is provided to the user for display on the user interface. If the user wants to alter the input data at 1316, the process continues at 1306. Otherwise, the process stops at 1318.

Figure 14:
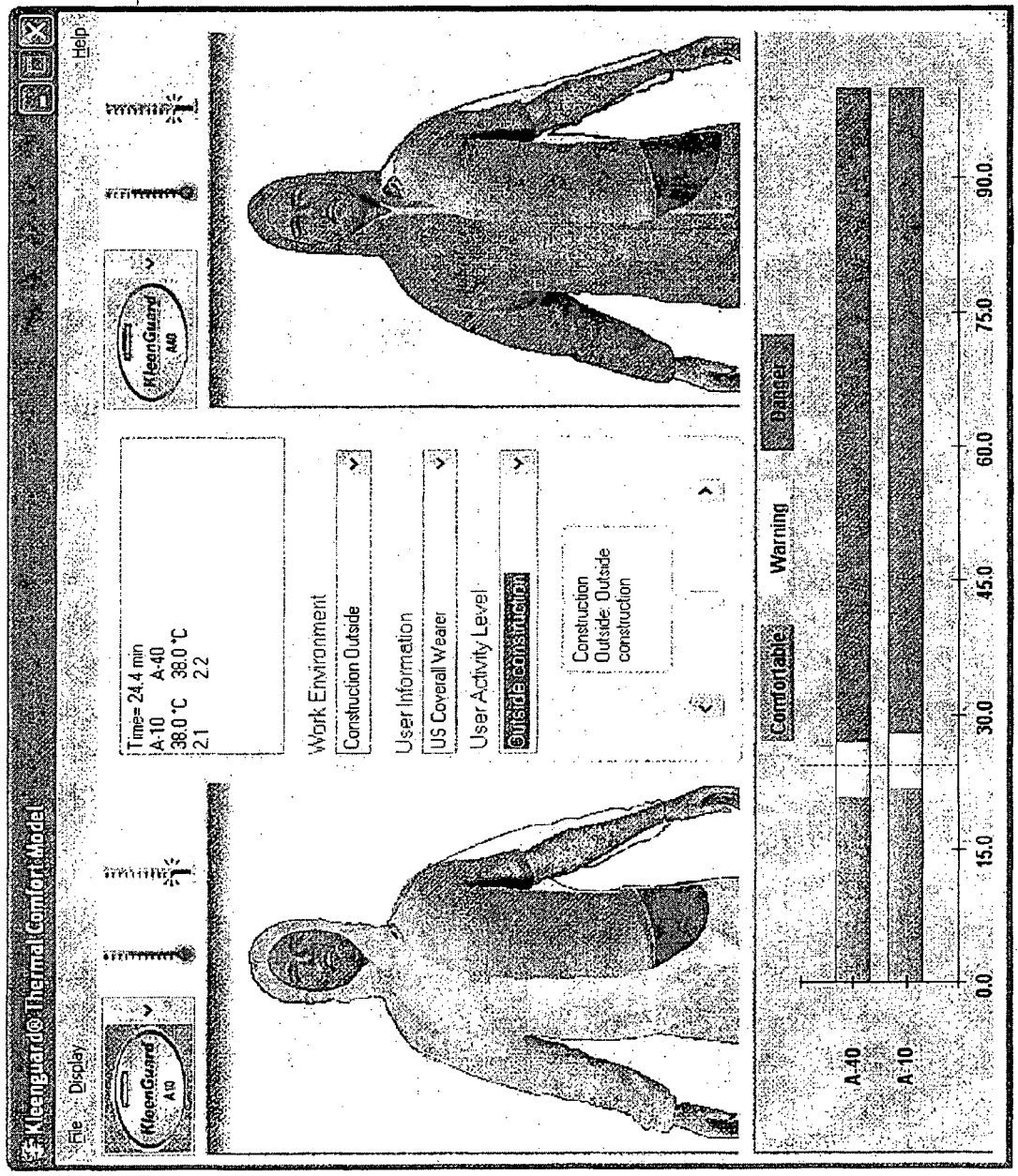
FIG. 14 is an exemplary user interface showing a side-by-side comparison of different garments.

Referring next to FIG. 14, an exemplary user interface 1402 shows a side-by-side comparison of different garments modeled on a human subject. A portion of the user interface 1402 identifies the particular garments modeled, the duration for model execution, ambient air temperature, air speed, a work environment, user information, and user activity level. The gap between the fabric layers is exposed on the visual representation of the human subject. The visual representation includes any representation capable of indicating thermal comfort anywhere on the spectrum of representation from photo-realistic representations to cartoon (e.g., anthropomorthic). A chart on the user interface 1402 is used to indicate the predicted thermal comfort level of each garment. In an embodiment, chart is color-coded corresponding to the comfort levels such as "comfortable," "warning," and "danger" over time. The thermal strain is also reflected in the visual representation of the human subject. In an embodiment, the visual representation of the subject is updated to refer to the thermal strain of the subject at a user specified time. In an embodiment, an alert such as a visual or audio alert is provided to the user when the comfort level exceeds a predefined (e.g., user-defined) threshold.

In the example of FIG. 14, the air temperature is represented by the background color, the temperature of any radiant heat/cool source is represented by the bar above the head of each subject represents, the microclimate temperature (e.g., temperature of the space between the subject and the outer garment) is represented by the color of the air gap, the temperature of the subject is represented by skin color, and the overall thermal comfort is represented by the facial expression on the subject (e.g., smile, frown, grimace, and the like). Further, the predicted perspiration rate of the subject is indicated graphically as perspiration (e.g., a quantity of beads of sweat) on the subject or the garment. The microclimate area is shown as a "cutaway" view of the garment on the subject. If the thermal strain determination yields a value that exceeds a particular threshold (e.g., pre-defined or user-defined), the eyes of the subject are shown as crossed-out. Exemplary thresholds include a high temperature (e.g., greater than 38 degrees Celsius) or dehydration (e.g., greater than 5% body mass has been lost).

With the first and second visual representations of the human subject in FIG. 14, the user interface 1402 enables the user to compare different garment combinations exposed to the same conditions (e.g., subject data and environmental or working conditions). Aspects of the invention enable the user to identify differences between garments and market one particular garment over the other based on the identified differences.

For example, in FIG. 14, a user conducts a side-by-side comparison of the KLEENGUARD® A10 Coveralls to the KLEENGUARD® A40 Coveralls, both available from the Kimberly-Clark Corporation, Roswell, Ga.

Figure 15:
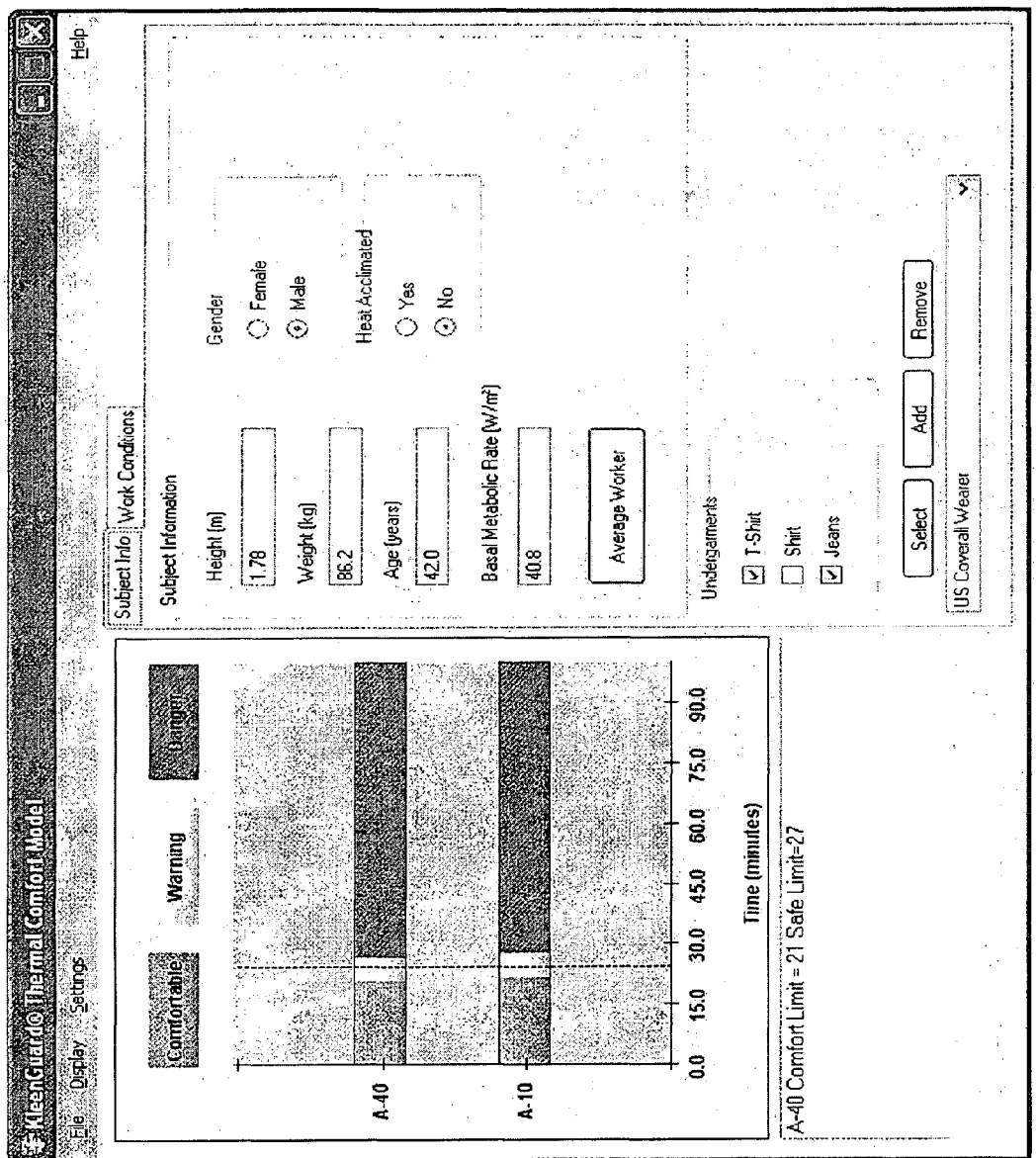
FIG. 15 is an exemplary user interface showing fields for entry of subject data by a user.

Referring next to FIG. 15, an exemplary user interface 1502 shows fields for entry of subject data by a user. The user interface 1502 includes fields for entry of height and weight of the subjects along with a basal metabolic rate. In an embodiment, the height and weight are used to determine the basal metabolic rate and skin surface areas. Other user-specific parameters are within the scope of the invention such as gender and whether the user is acclimated to the heat. For example, the exemplary thermal comfort model may account for body shape to allocate heat distribution to portions of the subject. The user interface 1502 also includes fields for identifying the undergarments worn by the subject.

The "US Coverall Wearer" selection represents a set of input parameters (e.g., height, weight, basal metabolic rate, undergarment choices, and the like). The input parameters include, for example, standard, predefined, or default inputs or input sets. In an embodiment, a plurality of sets of input parameters is available for selection by the user.

Figure 16:
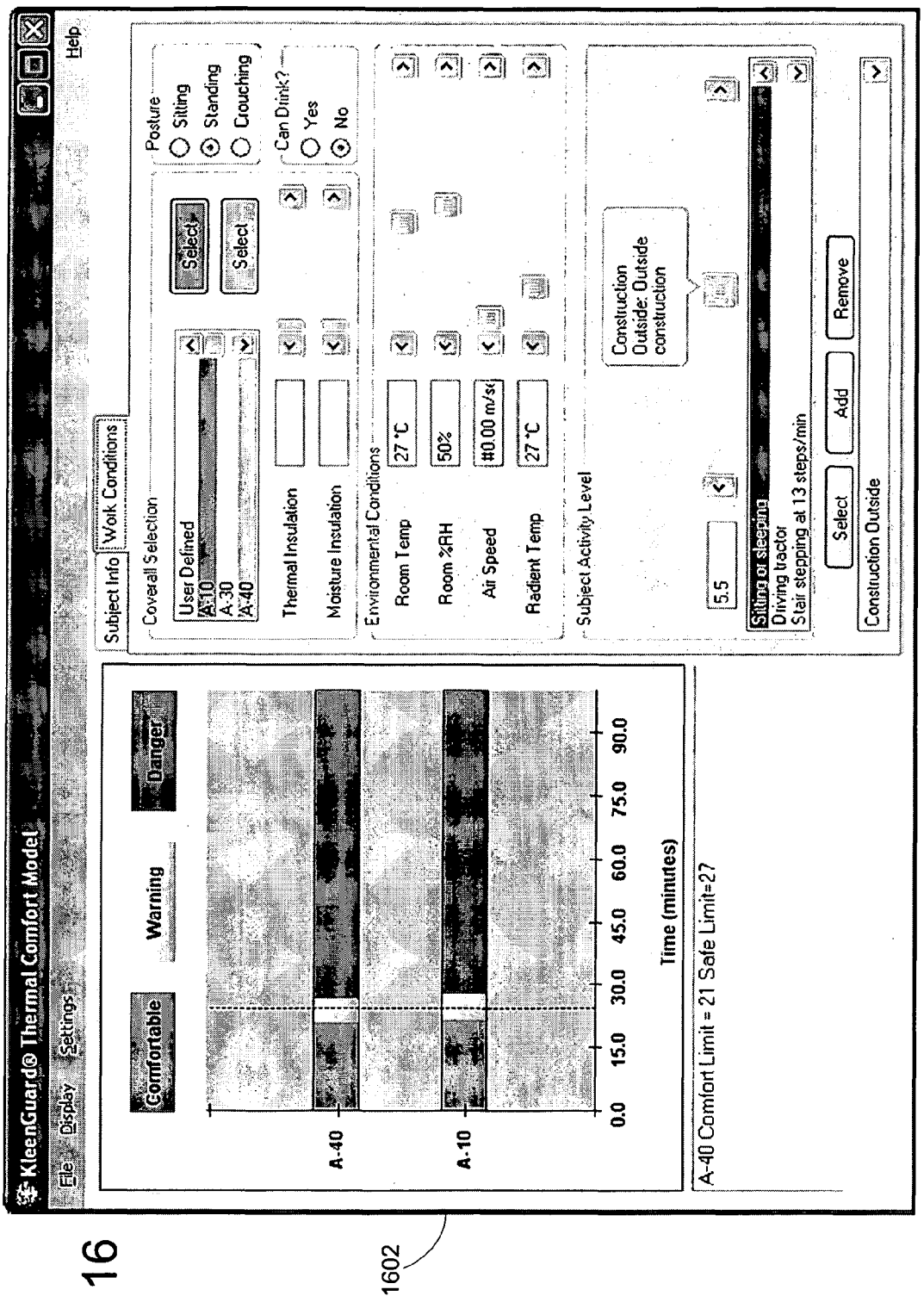
FIG. 16 is an exemplary user interface showing fields for entry of work conditions by the user.

Referring next to FIG. 16, an exemplary user interface 1602 shows fields for entry of work conditions by the user. The user interface 1602 includes fields for entry of a garment selection (e.g., fabric data), subject posture, re-hydration availability, thermal insulation, moisture insulation, environmental conditions such as room temperature and humidity, and the activity level of the subject. Aspects of the invention provide predefined activity levels. The user may modify the predefined activity levels or define or configure new activity levels. The "Construction Outside" selection represents a set of input parameters regarding the work environment and other environmental conditions. In an embodiment, a plurality of sets of input parameters is available for selection by the user.

ADDITIONAL EXAMPLES

Exemplary input data for a model according to embodiments of the invention is shown below in Table 1.

TABLE 1

Exemplary Input Data.

| Environment | | | |
|---|---|---|---|
| Out Temp (° C.) | 18.5 | initial MC Temp(° C.) | 16 |
| Outside Relative Humidity (%) | 67% | initial MC % RH | 70% |
| Radiant Temperature (° C.) | 21.1 | | |
| Exchange air Temp (° C.) | 16.0 | | |
| Exchange air RH (%) | 70% | | |
| User Information | | | |
| Alpha Msk/Mtot | 0.15 | Initial Skin Temp (° C.) | 33.7 |
| Body Mass (kg) | 86.2 | Initial Core Temp (° C.) | 36.8 |
| Height (m) | 1.78 | Age (years) | 30 |
| MET (W/m$^2$) | 44.7 | BMR (W/m$^2$) | 45.7 |
| Work Efficiency | 0.10 | Surface area (m$^2$) | 2.04 |
| Product Information | | | |
| Prod Ret (m$^2$ kPa/W) | 0.015 | | |
| Prod Rct (m$^2$ ° C./W) | 0.217 | | |
| Outside Air Velocity (m/s) | 1.0 | | |
| Prod Area (m$^2$) | 3.58 | | |
| Air exchange rate with outside (l/hr) | 0.0 | | |
| Volume of air in microclimate (l) | 30 | | |
| Velocity of air in microclimate (m/s) | 0.0 | hc_pr_i (W/m$^2$ K) | 10 |
| | | hc_pr_o (W/m$^2$ K) | 8.60 |
| Prod Fabric Basis Weight (g/m$^2$) | 67 | | |
| Prod Fabric Density (g/cm$^3$) | 0.12 | | |
| Prod Fiber Type | PP | | |
| Prod Fiber moisture level (g-H2O/g-wet fiber) | 0% | Prod Initial Temp | 25.0 |
| Prod Fabric emissivity | 0.98 | Prod Initial % RH | 10% |

TABLE 1-continued

Exemplary Input Data.

Undergarments

| | | | |
|---|---|---|---|
| Ug Ret (m² kPa/W) | 0.017 | | |
| Ug Rct (m² °C./W) | 0.228 | | |
| Ug Gap (cm) | 2.1 | | |
| Ug Area (m²) | 2.21 | hc_un_i (W/m² K) | 7.4 |
| Ug Fabric Basis Weight (g/m²) | 419 | hc_un_o (W/m² K) | 8.60 |
| Ug Fabric Density (g/cm³) | 0.68 | | |
| Ug Fiber Type | Cotton | | |
| Ug Fiber moisture level (g-H2O/g-wet fiber) | 6.46 | Ug Initial Temp | 30.0 |
| Ug Fabric emissivity | 0.98 | Ug Initial % RH | 10% |

Appendix B provides a description of the input parameters.

Exemplary input and output parameters and data are shown in Appendix A. In particular, an output file from a model according to an embodiment of the invention includes all the information from an input file, but adds time dependent data. In the example in Appendix A, the element Static_Vars includes all the basic properties of the model that do not change with time and includes sub-nodes for Subject, Environment, and Clothing. The element Dynamic_Vars includes all the time nodes (e.g., the state of the model at specific times). The Dynamic_Vars element contains a set of TimeData nodes. The first TimeData node has a Type attribute set to 'Initial' and indicates the initial values for each of the dynamic parameters in the model. Subsequent TimeData nodes with Type attributes set to 'Run' are output results from the model and represent the state of the model at a time indicated by the ModelTime subnode.

Alternately, input parameters may be time dependent. Such input data sets would change one or more of the model parameters to represent for example changes occurring in work environment, clothing type, or activity level. One method for implementing this type of input flexibility uses a single data format for input and output data sets. The resulting output data from running the model can be used as input data for a subsequent model input data set. Changes can be made to a single input parameter or set of input parameters model an instantaneous change in the state of the model. Concatenation of the outputs of each model run then simulates the condition when a model parameter changes.

The Summary element includes result calculations from the end of the model. The element Limit_50 represents the time it took for the subject to lose 50% of the acceptable water loss value. The element Limit_95 represents the time it took to lose 95% of the water value. The element Limit_Tre represents the time it took for the subject to reach 38° C. core body temperature. The element Limit_Comf represents the time it took for the subject to reach "2" (e.g., Very Hot) on the thermal comfort scale. It will be appreciated that data for some or all of these elements may be represented in the user interfaces illustrated herein.

Exemplary Operating Environment

A computing device such as computing device 204 in FIG. 2 or a computer has one or more processors or processing units and a system memory. The computer typically has at least some form of computer readable media. Computer readable media, which include both volatile and nonvolatile media, removable and non-removable media, may be any available medium that may be accessed by computer. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information and that may be accessed by computer. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Wired media, such as a wired network or direct-wired connection, and wireless media, such as acoustic, RF, infrared, and other wireless media, are examples of communication media. Combinations of any of the above are also included within the scope of computer readable media.

The system memory includes computer storage media in the form of removable and/or non-removable, volatile and/or nonvolatile memory. The computer may operate in a networked environment using logical connections to one or more remote computers, such as a remote computer.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well known computing systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

In operation, a computer executes computer-executable instructions embodied in one or more computer-executable components stored on one or more computer-readable media to implement aspects of the invention described and/or illustrated herein.

The embodiments illustrated and described herein as well as embodiments not specifically described herein but within the scope of aspects of the invention constitute exemplary means for means for defining the model, exemplary means for predicting the thermal strain, exemplary means for simultaneously solving equations for conservation of energy and conservation of mass based on the received data, exemplary means for calculating a radiant heat exchange rate among the fabric layers independent of the gap, and exemplary means for accounting for air exchange between the gap and ambient air external to the garments.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

Appendix A

Listed below are extensible markup language (XML) data excerpts identifying exemplary input parameters and data along with exemplary output parameters and data for use with embodiments of the invention.

```
<?xml version="1.0" encoding="utf-8"?>
<MCModelInput d1p1:Name="Microclimate Model 2007" xmlns:d1p1="ns">
  <ModelInfo>
    <Creator>KCModel.vb</Creator>
    <Version>1.0.0.0</Version>
    <Date>2/18/2008 12:00:00 AM</Date>
    <Notes>computer generated results</Notes>
    <TimeStep Units="sec">0.01</TimeStep>
    <RecordStep Units="sec">60</RecordStep>
    <Duration Units="sec">8000</Duration>
  </ModelInfo>
  <Static_Vars>
    <Subject>
      <Description>Subject 3 wearing product A in 60 °F 50.0% RH</Description>
      <Mass Units="kg">73.463</Mass>
      <Height Units="m">173.355</Height>
      <Age Units="Years">33</Age>
      <BMR Units="W/m2">39.1574587314438</BMR>
      <Surface_Area Units="m2">1.87358919834702</Surface_Area>
      <Heat_Acclimated Units="Percent">0</Heat_Acclimated>
      <Gender Units="Male / Female">2</Gender>
      <Posture Units="Description">standing</Posture>
      <WalkSpeed Units="m/s">0</WalkSpeed>
      <Wind_Angle Units="degrees">0</Wind_Angle>
      <Can_Drink Units="Y or N">N</Can_Drink>
    </Subject>
    <Environment>
      <Description>Chamber at 60 °F and 50.0% Relative Humidity</Description>
    </Environment>
    <Clothing>
      <Description />
      <Coverage Units="Percent">1.0</Coverage>
    </Clothing>
  </Static_Vars>
  <Dynamic_Vars>
    <TimeData Type="Initial">
      <ModelTime Units="sec">.000</ModelTime>
      <ModelState>
```

```
<Subject>
  <Activity Units="METS">1.00</Activity>
  <Work_Efficiency Units="Percent">0.100</Work_Efficiency>
  <Temp_Skin Units="°C">31.82</Temp_Skin>
  <Temp_Core Units="°C">37.21<Temp_Core>
  <Q_Respiration Units="W/m²">0.0</Q_Respiration>
  <Q_Storage Units="W/m²">39.2</Q_Storage>
  <Q_Evaporation Units="W/m²">0.0</Q_Evaporation>
  <Q_Convection Units="W/m²">0.0</Q_Convection>
  <Q_Radiation Units="W/m²">0.0</Q_Radiation>
  <Q_Conduction Units="W/m²">0.0</Q_Conduction>
  <Q_Sweat Units="W/m²">0.0</Q_Sweat>
  <M_Drip Units="g/m² hr">0.0</M_Drip>
  <M_TEWL Units="g/m² hr">0.0</M_TEWL>
  <M_Sweat Units="g/m² hr">0.0</M_Sweat>
  <Total_H2O_Loss Units="g">0.0</Total_H2O_Loss>
  <SkinMassFrac Units="Percent">0.0</SkinMassFrac>
  <PMV Units="N/A">0.0</PMV>
</Subject>
<Environment>
  <Temp_Air Units="°C">16.7</Temp_Air>
  <Temp_Radient Units="°C">16.7</Temp_Radient>
  <RH_Air Units="Percent">0.545</RH_Air>
  <Temp_Exch_Air Units="°C">16.7</Temp_Exch_Air>
  <Air_Speed Units="m/s">0.1</Air_Speed>
</Environment>
<Clothing>
  <Undergarment>
    <Fabric>
      <Fiber_Type>1</Fiber_Type>
      <Basis_Weight Units="g/m²">250</Basis_Weight>
      <Density Units="g/cm³">0.24</Density>
      <Moisture_Content Units="g-H2O/g-total">0.282764478695559</Moisture_Content>
      <Emissivity Units="unitless">0.95</Emissivity>
      <Rct Units="m² °C / W">0.1</Rct>
      <Ret Units="m² kPa / W">0.012</Ret>
      <Clo Units="Clo units">0.644</Clo>
      <Im Units="unitless">0.505</Im>
      <MOCON Units="g/m² day">19247</MOCON>
      <Temp Units="°C">31.83</Temp>
      <Relative_Humidity Units="Percent">1</Relative_Humidity>
      <Saturation Units="Percent">0.08</Saturation>
    </Fabric>
    <Surface_Area Units="m²">2.06</Surface_Area>
  </Undergarment>
  <Outergarment>
    <Fabric>
      <Fiber_Type>3</Fiber_Type>
      <Basis_Weight Units="g/m²">42.067</Basis_Weight>
      <Density Units="g/cm³">0.159</Density>
      <Moisture_Content Units="g-H2O/g-total">0.000150243691980493</Moisture_Content>
      <Emissivity Units="unitless">0.95</Emissivity>
      <Rct Units="m² °C / W">0.1178</Rct>
      <Ret Units="m² kPa / W">0.02224</Ret>
      <Clo Units="Clo units">0.758</Clo>
      <Im Units="unitless">0.321</Im>
      <MOCON Units="g/m² day">10385</MOCON>
      <Temp Units="°C">29.2</Temp>
      <Relative_Humidity Units="Percent">1</Relative_Humidity>
      <Saturation Units="Percent">2.88E−05</Saturation>
    </Fabric>
    <Surface_Area Units="m²">3.58</Surface_Area>
  </Outergarment>
  <MicroClimate>
    <Temp Units="°C">29.2</Temp>
    <Relative_Humidity Units="Percent">0.555</Relative_Humidity>
    <Air_Exchange_Rate Units="l/hr">0.000</Air_Exchange_Rate>
    <Volume Units="1">27.0</Volume>
    <Velocity Units="m/s">0.3</Velocity>
    <Surface_Area Units="m²">0.3</Surface_Area>
  </MicroClimate>
  <Transfer_Coefficients>
    <hc_out Units="W / m² °C">0.000</hc_out>
    <hr_out Units="W / m² °C">1.000</hr_out>
    <hc_um Units="W cm / m² °C">0.000</hc_um>
    <hc_mc Units="W cm / m² °C">0.000</hc_mc>
    <DiffC3 Units="g / sec cm kPa">1.000</DiffC3>
  </Transfer_Coefficients>
```

```
      <Im_Tot_Static Units="n/a">0.0</Im_Tot_Static>
      <Icl_Tot_Static Units="Clo">0.0</Icl_Tot_Static>
    </Clothing>
    <WaterLayers>
      <Skin_Undergarment>
        <Water_Mass Units="g">0.00000</Water_Mass>
        <Water_Area Units="m2">0.00010</Water_Area>
      </Skin_Undergarment>
      <Undergarment_Microclimate>
        <Water_Mass Units="g">0.00000</Water_Mass>
        <Water_Area Units="m2">0.00010</Water_Area>
      <Undergarment_Microclimate>
      <Microclimate_Coverall>
        <Water_Mass Units="g">0.38084</Water_Mass>
        <Water_Area Units="m2">0.00010</Water_Area>
      </Microclimate_Coverall>
      <Coverall_Outside>
        <Water_Mass Units="g">0.38</Water_Mass>
        <Water_Area Units="m2">0.00010</Water_Area>
      </Coverall_Outside>
    </WaterLayers>
  </ModelState>
</TimeData>
<TimeData Type="Initial">
  <ModelTime Units="sec">.000</ModelTime>
  <ModelState>
    <Subject>
      <Activity Units="METS">1.00</Activity>
      <Work_Efficiency Units="Percent">0.100</Work_Efficiency>
      <Temp_Skin Units="°C">31.82</Temp_Skin>
      <Temp_Core Units="°C">37.21</Temp_Core>
      <Q_Respiration Units="W/m2">0.0</Q_Respiration>
      <Q_Storage Units="W/m2">39.2</Q_Storage>
      <Q_Evaporation Units="W/m2">0.0</Q_Evaporation>
      <Q_Convection Units="W/m2">0.0</Q_Convection>
      <Q_Radiation Units="W/m2">0.0</Q_Radiation>
      <Q_Conduction Units="W/m2">0.0</Q_Conduction>
      <Q_Sweat Units="W/m2">0.0</Q_Sweat>
      <M_Drip Units="g/m2 hr">0.0</M_Drip>
      <M_TEWL Units="g/m2 hr">0.0</M_TEWL>
      <M_Sweat Units="g/m2 hr">0.0</M_Sweat>
      <Total_H2O_Loss Units="g">0.0</Total_H2O_Loss>
      <SkinMassFrac Units="Percent">0.0</SkinMassFrac>
      <PMV Units="N/A">0.0</PMV>
    </Subject>
    <Environment>
      <Temp_Air Units="°C">16.7</Temp_Air>
      <Temp_Radient Units="°C">16.7</Temp_Radient>
      <RH_Air Units="Percent">0.545</RH_Air>
      <Temp_Exch_Air Units="°C">16.7</Temp_Exch_Air>
      <Air_Speed Units="m/s">0.1</Air_Speed>
    </Environment>
    <Clothing>
      <Undergarment>
        <Fabric>
          <Fiber_Type>1</Fiber_Type>
          <Basis_Weight Units="g/m2">250</Basis_Weight>
          <Density Units="g/cm3">0.24</Density>
          <Moisture_Content Units="g-H2O/g-total">0.283</Moisture_Content>
          <Emissivity Units="unitless">0.95</Emissivity>
          <Rct Units="m2 °C / W">0.1</Rct>
          <Ret Units="m2 kPa / W">0.012</Ret>
          <Clo Units="Clo units">0.644052518592814</Clo>
          <Im Units="unitless">0.51</Im>
          <MOCON Units="g/m2 day">19247</MOCON>
          <Temp Units="°C">31.8228</Temp>
          <Relative_Humidity Units="Percent">1</Relative_Humidity>
          <Saturation Units="Percent">0.08</Saturation>
        </Fabric>
        <Surface_Area Units="m2">2.056</Surface_Area>
      </Undergarment>
      <Outergarment>
        <Fabric>
          <Fiber_Type>3</Fiber_Type>
          <Basis_Weight Units="g/m2">42.067</Basis_Weight>
          <Density Units="g/cm3">0.159</Density>
          <Moisture_Content Units="g-H2O/g-total">0.000150243691980493</Moisture_Content>
          <Emissivity Units="unitless">0.95</Emissivity>
          <Rct Units="m2 °C / W">0.1178</Rct>
```

```
      <Ret Units="m² kPa / W">0.02224</Ret>
      <Clo Units="Clo units">0.759</Clo>
      <Im Units="unitless">0.321</Im>
      <MOCON Units="g/m² day">10385</MOCON>
      <Temp Units="°C">29.2</Temp>
      <Relative_Humidity Units="Percent">1</Relative_Humidity>
      <Saturation Units="Percent">2.89E-05</Saturation>
     </Fabric>
     <Surface_Area Units="m²">3.59</Surface_Area>
    </Outergarment>
    <MicroClimate>
     <Temp Units="°C">29.2</Temp>
     <Relative_Humidity Units="Percent">0.555</Relative_Humidity>
     <Air_Exchange_Rate Units="l/hr">0.000</Air_Exchange_Rate>
     <Volume Units="l">27.0</Volume>
     <Velocity Units="m/s">0.3</Velocity>
     <Surface_Area Units="m²">0.3</Surface_Area>
    </MicroClimate>
    <Transfer_Coefficients>
     <hc_out Units="W / m² °C">0.000</hc_out>
     <hr_out Units="W / m² °C">1.000</hr_out>
     <hc_um Units="W cm / m² °C">0.000</hc_um>
     <hc_mc Units="W cm / m² °C">0.000</hc_mc>
     <DiffC3 Units="g / sec cm kPa">1.000</DiffC3>
    </Transfer_Coefficients>
    <Im_Tot_Static Units="n/a">0.0</Im_Tot_Static>
    <Icl_Tot_Static Units="Clo">0.0</Icl_Tot_Static>
   </Clothing>
   <WaterLayers>
    <Skin_Undergarment>
     <Water_Mass Units="g">0.00000</Water_Mass>
     <Water_Area Units="m²">0.00010</Water_Area>
    </Skin_Undergarment>
    <Undergarment_Microclimate>
     <Water_Mass Units="g">0.00000</Water_Mass>
     <Water_Area Units="m²">0.00010</Water_Area>
    </Undergarment_Microclimate>
    <Microclimate_Coverall>
     <Water_Mass Units="g">0.38084</Water_Mass>
     <Water_Area Units="m²">0.00010</Water_Area>
    </Microclimate_Coverall>
    <Coverall_Outside>
     <Water_Mass Units="g">0.38084</Water_Mass>
     <Water_Area Units="m²">0.00010</Water_Area>
    </Coverall_Outside>
   </WaterLayers>
  </ModelState>
 </TimeData>
 <TimeData Type="Run">
  <ModelTime Units="sec">60.010</ModelTime>
  <ModelState>
   <Subject>
    <Activity Units="METS">1.00</Activity>
    <Work_Efficiency Units="Percent">0.100</Work_Efficiency>
    <Temp_Skin Units="°C">34.41</Temp_Skin>
    <Temp_Core Units="°C">36.79</Temp_Core>
    <Q_Respiration Units="W/m²">4.5</Q_Respiration>
    <Q_Storage Units="W/m²">34.7</Q_Storage>
    <Q_Evaporation Units="W/m²">0.0</Q_Evaporation>
    <Q_Convection Units="W/m²">30.8</Q_Convection>
    <Q_Radiation Units="W/m²">0.0</Q_Radiation>
    <Q_Conduction Units="W/m²">0.0</Q_Conduction>
    <Q_Sweat Units="W/m²">0.0</Q_Sweat>
    <M_Drip Units="g/m² hr">0.0</M_Drip>
    <M_TEWL Units="g/m² hr">0.0</M_TEWL>
    <M_Sweat Units="g/m² hr">0.0</M_Sweat>
    <Total_H2O_Loss Units="g">0.2</Total_H2O_Loss>
    <SkinMassFrac Units="Percent">0.1</SkinMassFrac>
    <PMV Units="N/A">2.4</PMV>
   </Subject>
   <Environment>
    <Temp_Air Units="°C">16.7</Temp_Air>
    <Temp_Radient Units="°C">16.7</Temp_Radient>
    <RH_Air Units="Percent">0.545</RH_Air>
    <Temp_Exch_Air Units="°C">16.7</Temp_Exch_Air>
    <Air_Speed Units="m/s">0.1</Air_Speed>
   </Environment>
   <Clothing>
    <Undergarment>
     <Fabric>
```

```xml
      <Fiber_Type>1</Fiber_Type>
      <Basis_Weight Units="g/m2">250</Basis_Weight>
      <Density Units="g/cm3">0.24</Density>
      <Moisture_Content Units="g-H2O/g-total">0.280</Moisture_Content>
      <Emissivity Units="unitless">0.95</Emissivity>
      <Rct Units="m2 °C / W">0.1</Rct>
      <Ret Units="m2 kPa / W">0.012</Ret>
      <Clo Units="Clo units">0.644</Clo>
      <Im Units="unitless">0.505</Im>
      <MOCON Units="g/m2 day">19247</MOCON>
      <Temp Units="°C">32.9</Temp>
      <Relative_Humidity Units="Percent">1</Relative_Humidity>
      <Saturation Units="Percent">0.079</Saturation>
     </Fabric>
     <Surface_Area Units="m2">2.055</Surface_Area>
    </Undergarment>
    <Outergarment>
     <Fabric>
      <Fiber_Type>3</Fiber_Type>
      <Basis_Weight Units="g/m2">42.067</Basis_Weight>
      <Density Units="g/cm3">0.159</Density>
      <Moisture_Content Units="g-H2O/g-total">5.10E-05</Moisture_Content>
      <Emissivity Units="unitless">0.95</Emissivity>
      <Rct Units="m2 °C / W">0.1</Rct>
      <Ret Units="m2 kPa / W">0.012</Ret>
      <Clo Units="Clo units">0.644</Clo>
      <Im Units="unitless">0.505</Im>
      <MOCON Units="g/m2 day">19247</MOCON>
      <Temp Units="°C">29.9</Temp>
      <Relative_Humidity Units="Percent">0.335</Relative_Humidity>
      <Saturation Units="Percent">9.81E-06</Saturation>
     </Fabric>
     <Surface_Area Units="m2">3.58</Surface_Area>
    </Outergarment>
    <MicroClimate>
     <Temp Units="°C">30.9</Temp>
     <Relative_Humidity Units="Percent">0.652</Relative_Humidity>
     <Air_Exchange_Rate Units="l/hr">0.000</Air_Exchange_Rate>
     <Volume Units="l">27.0</Volume>
     <Velocity Units="m/s">0.3</Velocity>
     <Surface_Area Units="m2">0.3</Surface_Area>
    </MicroClimate>
    <Transfer_Coefficients>
     <hc_out Units="W / m2 °C">3.312</hc_out>
     <hr_out Units="W / m2 °C">1.000</hr_out>
     <hc_um Units="W cm / m2 °C">0.662</hc_um>
     <hc_mc Units="W cm / m2 °C">0.662</hc_mc>
     <DiffC3 Units="g / sec cm kPa">1.000</DiffC3>
    </Transfer_Coefficients>
    <Im_Tot_Static Units="n/a">0.0</Im_Tot_Static>
    <Icl_Tot_Static Units="Clo">0.0</Icl_Tot_Static>
   </Clothing>
   <WaterLayers>
    <Skin_Undergarment>
     <Water_Mass Units="g">0.00000</Water_Mass>
     <Water_Area Units="m2">0.00010</Water_Area>
    </Skin_Undergarment>
    <Undergarment_Microclimate>
     <Water_Mass Units="g">0.00000</Water_Mass>
     <Water_Area Units="m2">0.00010</Water_Area>
    </Undergarment_Microclimate>
    <Microclimate_Coverall>
     <Water_Mass Units="g">0.00000</Water_Mass>
     <Water_Area Units="m2">0.00010</Water_Area>
    </Microclimate_Coverall>
    <Coverall_Outside>
     <Water_Mass Units="g">0.00012</Water_Mass>
     <Water_Area Units="m2">0.00012</Water_Area>
    </Coverall_Outside>
   </WaterLayers>
  </ModelState>
</TimeData>
```

-continued

```
[The remaining TimeData Nodes would be included at this point in the document]
  </Dynamic_Vars>
  <Summary>
    <Limit_50 Units="min">0.0</Limit_50>
    <Limit_95 Units="min">0.0</Limit_95>
    <Limit_Tre Units="min">0.0</Limit_Tre>
  </Summary>
</MCModelInput>
```

Appendix B

Listed below are descriptions of the terms used in TABLE 1 and refer in general to input parameters for the model.

Description of Terms

Out Temp (° C.): The temperature of the air in the environment where the subject is being evaluated Outside Relative Humidity (%): The relative humidity of the air in the environment where the subject is being evaluated Radiant Temperature (° C.): The temperature of a radiant heat source or sink. When no such source exists this is the same as Out Temp.

Exchange air Temp (° C.): The temperature of air that is exchanged with the inside air layers. Unless there is some other source of air to the layer this is the same as Out Temp.

Exchange air RH (%): The relative humidity of air that is exchanged with the inside air layers. Unless there is some other source of air to the layer this is the same as Outside Relative Humidity.

Alpha Msk/Mtot: The fraction of the body mass that is in the skin layer.

Body Mass (kg): The nude body mass of the subject.

Height (m): The height of the subject.

MET (W/m$^2$): The metabolic energy production of the subject. This corresponds to the rate of energy being generated by the subject and changes as a function of the activity.

Work Efficiency The efficiency of the subject at converting metabolic energy into work done by the body. This is the ratio of work done by the body to the MET.

Prod Ret (m$^2$ kPa/W): The moisture insulation of the outer garment layer. Fabric with an Ret of 0.5 would allow enough moisture to pass through one square meter of fabric when the vapor pressure gradient across the fabric was 1 kilopascal that if the water had evaporated, two watts of heat would be removed from the underlying layer. Moisture insulation can be measured for example using sweating mannequins.

Prod Rct (m$^{2o}$ C./W): The thermal insulation of the outer garment layer. Fabric with an Rct value of 0.5 would allow two watts of heat to pass through one square meter of the fabric when the temperature gradient across the fabric was one degree Celsius. Thermal insulation can be measured for example using sweating mannequins.

Outside Air Velocity (m/s): The speed that the environmental air moves across the surface of the outer fabric layer.

Prod Area (m$^2$): The surface area of the outer fabric layer.

Air exchange rate with outside (l/hr): The rate that air is moved from the environment into the air layer between fabric layers. A value of one liter per hour means that one liter of the air layer air is replaced by one liter of the outside air per hour.

Volume of air in microclimate (l): The volume of air in the gap between the undergarment and the outer garment.

Velocity of air in microclimate (m/s): The speed of the air layer in the gap between the fabric layers relative to the fabric layer surfaces.

Prod Fabric Basis Weight (g/m$^2$): The dry mass per unit area for the outer fabric layer.

Prod Fabric Density (g/cm$^3$): The mass per unit volume of the outer fabric layer. It is the ratio of the fiber mass excluding absorbed water to the volume of the outer fabric layer in its use state.

Prod Fiber Type: The type of fiber that makes up the outer fabric layer. This specifies which sorption isotherm data is used in the calculations of moisture and heat movement within the fabric.

Prod Fiber moisture level (g-H2O/g-wet fiber): The mass of water that has been absorbed into the fiber making up the outer fabric layer. The moisture level is the ratio of the absorbed water to the total weight of the wet fiber.

Prod Fabric emissivity: The emissivity of the outer fabric layer. This is used in the calculation of heat exchange from radiant heat exchange between layers and should represent the average emissivity for the relevant wavelengths.

Ug Ret (m$^2$ kPa/W): The moisture insulation of the undergarment layer. See Prod Ret for more information. Moisture insulation can be measured for example using sweating mannequins.

Ug Rct (m$^{2o}$ C./W): The thermal insulation of the undergarment layer. See Prod Rct for more information. Thermal insulation of fabric layers can be measured for example using sweating mannequins.

Ug Gap (cm): The average distance between the undergarment fabric layer and the outer fabric layer.

Ug Area (m$^2$): The total surface area of the undergarment fabric layer.

Ug Fabric Basis Weight (g/m$^2$): The dry mass per unit area for the undergarment fabric layer.

Ug Fabric Density (g/cm$^3$): The mass per unit volume of the outer fabric layer. It is the ratio of the fiber mass excluding absorbed water to the volume of the outer fabric layer in its use state.

Ug Fiber Type: The type of fiber that makes up the undergarment fabric layer. This specifies which sorption isotherm data is used in the calculations of moisture and heat movement within the fabric.

Ug Fiber moisture level (g-H2O/g-wet fiber): The mass of water that has been absorbed into the fiber making up the undergarment fabric layer. The moisture level is the ratio of the absorbed water to the total weight of the wet fiber.

Ug Fabric emissivity: The emissivity of the undergarment fabric layer. The emissivity of most clothing fabrics is very close to unity. This property can readily be measured using methods described in the art.

initial MC Temp (° C.): The initial temperature of the air layer between the fabric layers.

initial MC % RH: The initial relative humidity of the air layer between fabric layers.

Initial Skin Temp (° C.): The initial average temperature of the subjects skin.
Initial Core Temp (° C.): The initial average core temperature of the subject.
Age (years): The age of the subject.
BMR (W/m$^2$): The basal metabolic rate of the subject.
Surface area (m$^2$): The total surface area of the subjects skin.
hc_pr_i (W/m$^2$ K): The convective transfer coefficient at the boundary between the air layer and the outer fabric layer. Various methods may be employed to estimate this transfer coefficient including experimentation.
hc_pr_o (W/m$^2$ K): The convective transfer coefficient at the boundary between the outer fabric layer and the outside environment. Various methods may be employed to estimate this transfer coefficient. Several published articles describe empirical models of this transfer coefficient
Prod Initial Temp: The initial temperature of the outer garment fabric layer.
Prod Initial % RH: The initial relative humidity of the air between the fibers that make up the product fabric layer.
hc_un_i (W/m$^2$ K): The convective transfer coefficient at the boundary between the undergarment and the subjects skin. Various methods may be employed to estimate this transfer coefficient including experimentation.
hc_un_o (W/m$^2$ K): The convective transfer coefficient at the boundary between the undergarment and the air layer between the undergarment and the outer garment fabric layers. Various methods may be employed to estimate this transfer coefficient including experimentation.
Ug Initial Temp: The initial temperature of the undergarment fabric layer.
Ug Initial % RH: The initial relative humidity of the air between the fibers that make up the undergarment fabric layer.

Appendix C

Listed below is Mathematica code describing the equations used to calculate the heat and moisture fluxes described in FIG. 5.

In[112]:=Const={ad1→3.485, ad2→1.31838, ad3→1000, ad4→274.15, sp1→0.6112, sp2→17.62, sp3→243.12, sh1→0.6217, sh2→0.3783, Ptot→101.325, C1 → 0.67454, C2 →0.01, C3→0.00000162, K1→1.0046, K2→1.84593, R→5.67×10$^{-6}$, k →273.15}
Out[112]=ad1 →3.485, ad2→1.31838, ad3→1000, ad4→274.15, sp1→0.6112, sp2→17.62, sp3→243.12, sh1→0.6217, sh2→0.3783, Ptot→101.325, C1→0.67454, C2→0.01, C3→1.62×10$^{-6}$, K1→1.0046, K2→1.84593, R→5.67×10$^{-8}$, k→273.15}
In[113]:=(*R the Stefan-Boltzman constant 5.67×10$^{-5}$ a W/m$^2$ K
In[114]:=(*k of 273.15, add this to ° C. to get Kelvin*)
In[115]:=(*C1 is the latent heat of vaporization for water=0.67454 (W hr/g)*)
In[116]:=(*The following are descriptions of functions used in the calculations*) =In[117]:=(*AirDen=Function for Air Density, Total pressure 'Ptot' in kPa, Partial pressure of water vapor 'PP in kPa, and Air Temp 'Temp' in ° C., provides air density in g/cm$^3$*)
In[118]:=AirDen[Ptot_, PP_, Temp_]:=(ad1*Ptot−ad2*PP)/(ad3*(Temp+ad4))
In[119]:=(*SatPress=Function for Saturated Vapor pressure at a specified temperature 'Temp' in ° C. provides saturated water vapor pressure in kPa*)
In[120]:=SatPress[Temp_]:=Sp1*Exp[Temp*sp2/(Temp*sp3)]
In[ 121]:=(*SpecHum=Function for Specific Humidity, Partial pressure 'PP' in kPa, and Total Pressure 'Ptot' in kPa, provides specific humidity in g-H20/g-total*)
In[122]:=SpecHum [PP_, Ptot_]:=Sh1*PP/(Ptot−sh2*PP)
In[123]:=(*QFab=Function for heat flux through a fabric layer due to conduction. Rct is the thermal insulation in a n=° C./W, Temperature at one surface 'T1' and temperature at the other surface 'T2' are temperatures in ° C. and 0 is in W/m$^2$*)
In[124]:=(QFab [Rct_, T1_, T2_] :=(T1−T2)/Rct
In[125]:=(*Qair Function for heat flux across a stagnant air gap. 'Tc' is thermal conductivity of air in W/cm−° C. at 0.00024, 'h' is the air space gap in cm provides heat flux in W/cm$^2$. Alternately Tc can be 24 W−cm/m$^2$ ° C. so Qair is in W/m$^2$*)
In[126]:=Qair[Tc_, T1_, T2_, h_]:=Tc*(T1−T2)/h
In[127]:=(*Qbound=Function for heat flux due to convection. 'hc' is the boundary layer transfer coefficient in W/m$^2$−° C. 'T1' is the temperature at one boundary in ° C. T2' is the temperature at the other boundary in. ° C.)
In[128]:=Qbound[hc, T1_, T2_] :=hc(T1−T2)
In[129]:=(*QFabWet=Function for heat flux due to evaporative loss as moisture evaporates and moves through a fabric. The moisture insulation 'Ret' in m$^2$ kPa /w, V1' is the vapor pressure at the evaporating surface in kPa and 'V2' the vapor pressure of the air on the other side of the fabric in kPa provides Qfabwet=W/m$^2$*)
In[130]:=QFabWet[Ret_, V1_, V2_]:=(V1−V2)/Ret
In[131]:=(*MFabWet=Function for water flux through a fabric. MFabWet is mass flux in g/m$^2$ hr*)
In[132]:=MFabWet[Ret_, V1_, V2_, C1_]:=FabWet[Ret, V1, V2]/C1
In[133]:=(*QboundWet=Heat flux from moisture evaporating from a surface into an open air space with transfer coefficient hd wm$^{2o}$ C.). LR is the lewis relation between heat and moisture transfer coefficients and approximately 16.5° C./kPa'V1' is the vapor pressure at the evaporating surace in kPa and V2' is the vapor pressure at the outside boundary in kPa. Provides heat flux in W/m$^2$*)
In[134]:=QboundWet[hc_, LR_, V1_, V2_]:=(V1−V2)*(hc*LR)
In[135]:=(*MboundWet=Moisture flux from evaporation into open air corresponding to the heat flux QboundWet[ ]provides moisture flux in g/m$^2$ hr *)
In[136]:=MoundWet[hc_, LR_, V1_, V2_, C1_]:=QboundWet[hc, LR, V1, V2]/C1
In[137]:=(*QRad=Heat flux from radiant heat exchange between two surfaces. 'T1' is the temperature of one surface in ° C., 'T2' is the temperature of the other surface in ° C. 'Em' is the emissivity of the emitting surface. 'Aratio' is the ratio of the surface areas. Heat flux is provided in W/m$^2$*) (*the view factor F12 is the fraction of radiation from surface 1 that is directly intercepted by surface 2. This value is 1 for the undergarment, and is the ratio of the undergarment surface area 'surface 1' to the outer garment surface area 'surface 2' when calculating the flux being absorbed into the outer surface '2'. Bird Stewart & Lightfoot pg 440*)
In[138]:=QRad[T1_, T2_, Em_, Aratio_]:=R*Ern*Aratio*((T1+k)^4−(T2+k)^4)
In[139]:=(*Qrd=Function of Heat flux from radient heat exchange between two surfaces. This uses a "transfer coefficient" type approach. Results are in W/m$^2$*)
In[140]:=Qrd[hr_, T1_, T2_]:=hr*(T1−T2)
In[141]:=(*hrad=function for radiant heat flux transfer coefficient calculation in W/m$^{2o}$ C.*)
In[142]:=hrad[ema_, T1_, T2_, k, R]:=ema*R*((T1+T2)/2+k)^3
In[143]:=(*QExch=Function for heat flux calculations for bringing in air of a known vapor pressure and temperature. AirDensity in g/cm$^2$. Specific Heat in J/g K. Temperature in ° C. Exchange Rate in cm$^2$/sec. provides Heat exchange in Watts*)

In[144]:=QExch[MCArDen_, MCSpecHeat_, MCTemp_, OutAirDen_, OutSpecHeat_, OutTemp_, ExchRate_]:=ExchRate*(MCAirDen*MCSpecHeat*MCTemp−OutAirDen*OutSpecHeat*Out Temp)

In[145]:=(*MExch=Function for water vapor mass flux as air is exchanged between the microclimate air and the outside air. microclimate air density 'MCAirDen' in g/cm². Microclimate specific humidity 'MCSpecHum' in g-water / g-total. Outside air density 'OutAirDen' in g/cm2. Outside air specific humidity 'OutSpecHum' in g-water / g-total. Air exchange rate 'ExchRate' in cm³ /sec provides water mass exchange rate in g/sec*)

In[146]:=MExch[MCAirDen_, MCSpecHum_, OutAirDen_, OutSpecHum_, ExchRate_]:=ExchRate*(MCAirDen*MCSpecHum−OutAirDen*OutSpecHum)

In[147]:=(*SpecHeat=Function for specific heat of moist air. 'SpecHum' is the specific humidity of the air g-H20/g-total , Specific heat J/gK*)

In[148]:=SpecHeat [SpecHum]:=K1*(1−SpecHum)+K2*SpecHum

In[149]:=(*The following are descriptions of the specific flux calculations and terms*)

In[150]:=(*Heat flux from skin surface into the undergarment fabric, Heat flux in W/m²*)

In[151]:=QCui=QFab[Rctu/2, Tsk, Tu]

$$\text{Out}[151] = \frac{2(Tsk - Tu)}{RcTu}$$

In[152]:=(*Heat flux from the undergarment fabric to the inner air layer/undergarment interface, Heat flux in W/m²*)

In[153]:=QCuo=QFab[Rctu/2, Tu, Tuna]

$$\text{Out}[153] = \frac{2(Tu - Tum)}{Rctu}$$

In[154]:=(*Heat flux from the undergarment surface into the inner air layer, Heat flux in W/m²*)

In[155]:=QCmi=Qbound)[hcum, Tum, Tm]

Out[155]:=hcum(−Tm+Tum)

In[156]:=(*Heat flux from the air layer to the inner air layer/outer garment interface, Heat flux in W/m²*)

In[157]:=QCmo−Qbound[hcum, Tm, Imo]

Out[157]:=hcum(Tm−Tmc)

In[158]:=(*Heat flux from the inner air layer/outer garment interface into the outer garment fabric, Heat flux in W/m²*)

In[159]:=QCci=QFab[Rctc/2, Tmc, Tc]

$$\text{Out}[159] = \frac{2(-Tc + Tmc)}{Rctc}$$

In[160]:=(*Heat flux from the outer garment fabric to the outside air/outer garment fabric interface, Heat flux in W/m²*)

In[161]:=QCco=QFab[Rctc/2, Tc, Tco]

$$\text{Out}[161] = \frac{2(Tc - Tco)}{Rctc}$$

In[162]:=(*Heat flux from the outside air/outer garment fabric interface to the outside environmental air, Heat flux in W/m²*)

In[163]:=Qcei=Qbound[hcco, Tco, Tout]

Out[163]:=hcco(Tco−Tout)

In[164]:=(*Heat flux leaving the undergarment, W/m²*)

In[165]:=QRuc=QRad[Tum, Tmc, Emu, 1]

Out[165]=Emu R(−(k=Tmc)⁴+(k+Tum)⁴)

In[166]:=(*Heat flux from air being exchanged between the microclimate layer and the outside air, W/m²*)

In[167]:=QXmo=[QExch[AirDen[Ptot, Vm, Tm], SpecHeat[SpecHum[VM, Ptot]], Tm, AirDen[Ptot, Vout, Tout], SpecHeat[SpecHum[Vout, Ptot]], Tout, ExRate]

$$\text{Out}[167] = \left( \frac{Tin(ad1\,Ptot - ad2\,Vin)\left(\frac{K2\,sh1\,Vm}{Ptot - sh1\,Vm} + K1\left(1 - \frac{sh1\,Vm}{Ptot - sh1\,Vm}\right)\right)}{ad3(ad4 + Tm)} - \frac{Tout(ad1\,Ptot - ad2\,Vout)\left(\frac{K2\,sh1\,Vout}{Ptot - sh1\,Vout} + K1\left(1 - \frac{sh1\,Vout}{Ptot - sh1\,Vout}\right)\right)}{ad3(ad4 + Tout)} \right)$$

In[168]:=(*Heat flux between the outside surface of the outer garment layer to the outside radiant surface, W/m²*)

In[169]:=QRce=QRad[Tco, Trad, Emc, 1]

Out[169]:=Emc R(k+Tco)⁴−(k+Trad)⁴)

In[170]:=(Heat flux from any liquid water evaporating/condensing from the boundary between the undergarment and skin layers into the undergarment. W/m²*)

In[171]:=QEsu=QFabWet[Retu/2, SatPress[Tsk], Vu]

$$\text{Out}[171]^2 \frac{2\left(e^{\frac{sp2\,Tsk}{sp3+Tsk}}sp1 - Vu\right)}{Retu}$$

In[172]:=(*Heat flux from any water evaporating/condensing from the undergarment fabric to a liquid layer the boundary between the undergarment and the microclimate air layers. W/m²*)

In[173]:QEumd=QFabWet[Retu/2, Vu, SatPress[Tum]]

$$\text{Out}[173] = \frac{2\left(-e^{\frac{sp2\,Tum}{sp2+Tum}}sp1 + Vu\right)}{Retu}$$

In[174]:=(*Heat flux from any water evaporating/condensing from the mircorclimate air layer to a liquid layer at the boundary between the undergarment and the mircoclimate air layer. W/m²*)

In[175]:=QEumo=C1*MEumo $$\text{Out}[175] = hcum\,LR\left(e^{\frac{spt\,Tum}{spt+Tum}}sp1 - Vm\right)$$

In[176]:=(*Heat flux from any water evaporating/condensing from the microclimate air layer to a liquid layer at the boundary between the outer fabric layer and the microclimate air layer. W/m$^2$*)
In[177]:=QEmci=C1*MEmci $$\text{Out}[177] = hcum\ LR - \left(-e^{\frac{spt\ Tmc}{spt+Tmc}}sp1 - Vm\right)$$

In[178]:=(*Heat flux from any water evaporating/condensing from the outer garment fabric layer to a liquid layer at the boundary between the microclimate air layer and the outer garment fabric layer. W/m$^2$*)
In[179]:=QEmco=QFabWet[Retc/2, SatPress[Tmc], Vc]

$$\text{Out}[179] = \frac{2\left(-e^{\frac{spt\ Tmc}{spt+Tmc}}sp1 - Vc\right)}{Retc}$$

In[180]:=(*Heat flux from any water evaporating/condensing from the outer garment fabric layer to a liquid layer at the boundary between the outside air layer and the outer garment fabric layer. W/m$^2$*)
In[181]:=QEcei=QFabWet[Retc/2, Vc, SatPress[Teo]]

$$\text{Out}[181] = \frac{2\left(-e^{\frac{spt\ Tco}{spt+Tco}}sp1 - Vc\right)}{Retc}$$

In[182]:=(*Heat flux from any water evaporating/condensing from the outside air to a liquid layer at the boundary between the outside air layer and the outer garment fabric layer. W/m$^2$*)
In[183]:=QEceo=C1*MEceo $$\text{Out}[183] = hcco\ LR\left(e^{\frac{spt\ Tco}{spt+Tco}}spt - Vout\right)$$

In[184]:=(*Heat flux from any moisture evaporating from the skin as transpidermal water loss, water diffusing through the skin layer. W/m$^2$*)
In[185]:=QEst=C1*MEst
Out[185]=C1 mTEWL
In[186]:=(*Mass flux of water vapor from the boundary between the skin and undergarment fabric layers into the undergarment fabric. g/m$^2$*)
In[187]:=Mui=MFabWet[Retu/2, SatPress[Tsk], Vu, C1]

$$\text{Out}[187] = \frac{2\left(e^{\frac{spt\ Tsk}{spt+Tsk}}sp1 - Vu\right)}{C1\ Retu}$$

In[188]:=(*Mass flux of water vapor from the undergarment fabric to the boundary between the undergarment fabric and the microclimate air layer. g/m$^2$*)
In[189]:=Muo=MFabWet[Retu/2, Vu, Vum, C1]

$$\text{Out}[189] = \frac{2(Vu - Vum)}{C1\ Retu}$$

In[190]:=(*Mass flux of water vapor from the boundary between the undergarment fabric and layer and the microclimate layer into the microclimate air layer. g/m$^2$*)
In[191]:=Mmi=MboundWet[hcum, LR, Vum, Vm, C1]

$$\text{Out}[191] = \frac{hcum\ LR(-Vm + Vum)}{C1}$$

In[192]:=(*Mass flux of water vapor from the microclimate air layer onto the surface of the outer garment fabric layer. g/m$^2$ hr*)
In[193]:=Mmo=MboundWet[hcum, LR, Vm, Vmc, C1]

$$\text{Out}[193] = \frac{hcum\ LR(Vm - Vmc)}{C1}$$

In[194]:=(*Mass flux of water vapor from the boundary between the microclimate and the outer garment fabric layer into the outer garment fabric. g/m$^2$ hr*)
In[195]:=Mci=MFabWet[Retc/2, Vmc, Vc, C1]

$$\text{Out}[195] = \frac{2(-Vc + Vmc)}{C1\ Retc}$$

In[196]:=(*Mass flux of water vapor from the outer garment fabric layer onto the boundary between the outer garment fabric and the outside air. g/m$^2$ hr*)
In[197]:=Mco=MFabWet[Retc/2, Vc, Vco, C1]

$$\text{Out}[197] = \frac{2(Vc - Vco)}{C1\ Retc}$$

In[198]:=(*Mass flux of water vapor from the boundary between the outer garment fabric layer and the outside air into the outside air. g/m$^2$ hr*)
In[199]:=Mei=MboundWet[hcco, LR, Vco, Vout, C1]

$$\text{Out}[199] = \frac{hcco\ LR(Vco - Vout)}{C1}$$

In[200]:=(*Mass flux of water vapor diffusing through the skin surface. g/m$^2$ hr*)
In[201]:=Mest=mTEWL
Out[201]=mTEWL
In[202]:=(*Mass flux of water vapor as air is exchanged between the microclimate air lawyer and the outside air. g/sec*)
In[203]:=MXmo=MExch[AirDen[Ptot, Vm, Tm], SpecHum[Vm, Ptot], AirDen[Ptot, Vout, Tout], SpecHum[Vout, Ptot], ExRate]

$$\text{Out}[203] = ExRate\left(\frac{sh1Vm(ad1\ Ptot - ad2\ Vm)}{ad3(ad4 + Tm)(Ptot - sh2\ Vm)} - \frac{sh1\ Vout(ad1\ Ptot - ad2\ Vout)}{ad3(ad4 + Tout)(Ptot - sh2\ Vout)}\right)$$

In[204]:=(*Mass flux of water vapor evaporating/condensing from a liquid layer at the boundary between the subjects skin and the undergarment fabric into the undergarment fabric. g/m$^2$ hr*)
In[205]:=MEsu=QEsu/C1

$$\text{Out}[205] = \frac{2\left(e^{\frac{spt\,Tsk}{spt+Tsk}}sp1 - Vu\right)}{C1\,Retu}$$

In[206]:=(*Mass flux of water vapor from the undergarment fabric onto the boundary between the undergarment fabric and the microclimate air layer. g/m² hr*)
In[207]:=MEumi=MFabWet[Retu/2, Vu, SatPress[Tum], C1]

$$\text{Out}[207] = \frac{2\left(-e^{\frac{spt\,Tum}{spt+Tum}}sp1 + Vu\right)}{C1\,Retu}$$

In[208]:=(*Mass flux of water vapor evaporating/condensing from a liquid layer at the boundary between the undergarment fabric and the microclimate air into the microclimate air layer. g/m² hr*)
In[209]:=MEumo=MboundWet[hcum, LR, SatPress[Turn], Vm, C1]

$$\text{Out}[209] = \frac{hcum\,LR\left(e^{\frac{sp^2\,Tum}{sp^2+Tum}}sp1 + Vm\right)}{C1}$$

In[210]:=(*Mass flux of water vapor evaporating/condensing to/from a liquid layer at the boundary between the outer garment fabric and the microclimate air layer from the microclimate air. g/m² hr*)
In[211]:=MEmci=MboundWet[hcum, LR, Vm, SatPress[Tmc], C1]

$$\text{Out}[211] = \frac{hcum\,LR\left(-e^{\frac{sp^2\,Tmc}{sp^2+Tmc}}sp1 + Vm\right)}{C1}$$

In[212]:=(*Mass flux of water vapor evaporating/condensing from the liquid layer at the boundary between the microclimate and the outer garment fabric layer and into the outer garment fabric. g/m² hr*)
In[213]:=MEmco=MFabWet[Retc/2, SatPress[Tmc], Vc, C1]

$$\text{Out}[213] := \frac{2\left(e^{\frac{sp^2\,Tmc}{sp^2+Tmc}}sp1 + Vc\right)}{C1\,Retc}$$

In[214]:=(*Mass flux of water vapor from the outer garment fabric layer evaporating/condensing onto a liquid water layer at the boundary between the outer garment fabric layer and the outside air. g/m² hr*)
In[215]:=MEcei=MFabWet[Retc/2, Vc, SatPress[Tco], C1]

$$\text{Out}[215] = \frac{2\left(-e^{\frac{sp^2\,Tco}{sp^2+Tco}}sp1 + Vc\right)}{C1\,Retc}$$

In[216]:=(*Mass flux of water vapor from a water layer at the boundary between the outer garment fabric layer and the outside air into the outside air. g/m² hr*)
In[217]:=MEceo=MboundWet[hcco, LR, SatPress[Tco], C1]

$$\text{Out}[217] := \frac{hcco\,LR\left(e^{\frac{sp^2\,Tco}{sp^2+Tco}}sp1 + Vout\right)}{C1}$$

In[218]:=(*Now show the conversation equations*)
In[232]:=(*Au=surface area of the undergarment fabric (m²). Am=surface area of the microclimate air layer (m²). Ac=surface area of the outer garment fabric layer (m²). Su=percent saturation of the undergarment fabric (unitless). Alum=surface area of any liquid layer on the outside surface of the undergarment fabric (m²). Almc=surface area of any liquid layer on the inside surface of the outer garment fabric layer (m²). Alco=surface area of any liquid layer on the outside surface of the outer garment fabric layer (m²).*)

In[219]:=(*Conservation of heat between undergarment and microclimate. Heat is conserved when CQUM=0*)
In[220]:=CQUM=(Au*QCuo−Am*QCmi−Au*QRuc)−(Au*Su*C1*(MEumi−MEumo))

$$\text{Out}[220] = \frac{2\,Au(Tu - Tum)}{Rctu} - Am\,hcum(-Tm + Tum) -$$
$$Au\,Emu\,R(-(k + Tmc)^4 + (k + Tum)^4) -$$
$$Au\,Cl\,Su\left(-\frac{hcum\,LR\left(e^{\frac{sp^2\,Tum}{sp^2+Tum}}sp1 + Vm\right)}{C1} + \frac{2\left(-e^{\frac{sp^2\,Tum}{sp^2+Tum}}sp1 - Vu\right)}{C1\,Retu}\right)$$

In[221]:=(*Conservation of heat between the microclimate and the outer garment fabric layer. Heat is conserved when CQMC=0*)
In[222]:=CQMC=(Am*QCmo+Au*QRuc−Ac*QCci)−(Alum*C1*(MEmci−MEmco))

$$\text{Out}[222] = Am\,hcum(Tm - Tmc) -$$
$$\frac{2\,Ac(-Tc + Tmc)}{Rctc} + Au\,Emu\,R(-(k + Tmc)^4 + (k + Tum)^4) -$$
$$ALum\,C1\left(-\frac{2\left(e^{\frac{sp^2\,Tmc}{sp^2+Tmc}}sp1 - Vc\right)}{C1\,Retc} + \frac{hcum\,LR\left(-e^{\frac{sp^2\,Tmc}{sp^2+Tmc}}sp1 - Vm\right)}{C1}\right)$$

In[223]:=(*Conservation of heat between the outer garment fabric layer and the outside air. Heat is conserved when CQCO=0*)
In[224]:=CQCO=(Ac*QCco−Ac*QCei−Ac*QRce)−(Alco*C1*(MEcei−MEceo))

$$\text{Out}[224] := \frac{2\,Ac(Tc - Tco)}{Rctc} -$$
$$Ac\,hcco(Tco - Tout) - Ac\,Emc\,R((k + Tco)^4 - (k + Trad)^4) -$$
$$ALco\,C1\left(-\frac{2\left(e^{\frac{sp^2\,Tco}{sp^2+Tco}}Sp1 - Vc\right)}{C1\,Retc} + \frac{hcco\,LR\left(e^{\frac{sp^2\,Tco}{sp^2+Tco}}sp1 + Vm\right)}{C1}\right)$$

In[225]:=(*Conversation of mass*)
In[226]:=(*Water mass conservation at the undergarment fabric layer and the microclimate air layer. Water is conserved when CMUM=0*)
In[227]:=CMUM=(Au*Muo−Am*Mmd)−(Au*Su*(MEund−MEumo))

$$\text{Out}[227] = \\ -Au\ Su\left(-\frac{hcum\ LR\left(e^{\frac{sp^2 Tum}{sp^2+Tum}}sp1-Vm\right)}{C1}+\frac{2\left(-e^{\frac{sp^2 Tum}{sp^2+Tum}}sp1-Vu\right)}{C1\ Retu}\right)+ \\ \frac{2\ Au(Vu-Vum)}{C1\ Retu}-\frac{Am\ hcum\ LR(-Vm+Vm)}{C1}$$

In[226]:=(*Water mass conservation between the microclimate air layer and the outside garment fabric layer. Water is conserved when CMMC=0*)
In[229]:=CMMC=(Am*Mmo−Ac*Hci)−Almc*(MEmci−MEmco))

$$\text{Out}[229] = \\ -ALmc\left(-\frac{2\left(e^{\frac{sp^2 Tmc}{sp^2+Tmc}}sp1-Vc\right)}{C1\ Retc}+\frac{hcum\ LR\left(-e^{\frac{sp^3 Tmc}{sp^2+Tmc}}sp1+Vm\right)}{C1}\right)+ \\ \frac{Am\ hcum\ LR(Vm-Vmc)}{C1}-\frac{2\ Ac(-Vc+Vmc)}{C1\ Retc}$$

In[230]:=(*Water mass conservation between the outer garment fabric layer and the outside air. Water is conserved when CMCO=0*)
In[231]:=CMCO=(Ac*Mco—Ac*Mei)−(Alco*(MEcei−MEceo))

$$\text{Out}[231] = \frac{2\ Ac(Vc-Vco)}{C1\ Retc}- \\ ALco\left(\frac{2\left(-e^{\frac{sp^2 Tco}{sp^2+Tco}}sp1-Vc\right)}{C1\ Retc}-\frac{hcco\ LR\left(e^{\frac{sp^2 Tco}{sp^2+Tco}}sp1+Vout\right)}{C1}\right)- \\ \frac{Ac\ hcco\ LR(Vco-Vout)}{C1}$$

What is claimed is:

1. A method for modeling thermal comfort, said method comprising:
    defining a computerized model of a plurality of fabric layers on a subject to indicate thermal strain on the subject, said fabric layers having at least one gap therebetween;
    receiving, from a user, data corresponding to one or more input parameters for the defined model, wherein the one or more input parameters include environmental condition data;
    receiving, from a user, a selection of a work environment from a plurality of predefined work environments;
    executing the defined model based at least on the selected work environment;
    generating output parameter data as a function of the defined model and the received data, wherein the generated output parameter data represents a thermal strain on the subject; and
    providing the generated output parameter data to the user for evaluation of the thermal strain of the subject.

2. The method of claim 1, wherein generating the output parameter data comprises simultaneously solving equations for conservation of energy and conservation of mass based on the received data from the user.

3. The method of claim 1, wherein generating the output parameter data comprises calculating a radiant heat exchange rate among the plurality of fabric layers independent of the gap.

4. The method of claim 1, wherein defining the computerized model comprises accounting for air exchange between the gap and ambient air external to the fabric layers.

5. The method of claim 1, further comprising generating the input parameters by selecting from distribution functions representing at least one of a population of subjects, work environments, and product properties.

6. A system comprising:
    a computerized model of garments on a subject, said garments having at least one gap therebetween;
    a memory area for storing the computerized model and a plurality of predefined work environments; and
    a processor configured to execute computer-executable instructions for:
        receiving environmental condition data and one or more of subject data and garment data from a user;
        receiving a selection of one of the plurality of work environments from a user;
        executing the model stored in the memory area to predict thermal strain on the subject based on the received data and the selected work environment; and
        providing the predicted thermal strain to the user.

7. The system of claim 6, wherein the subject represents a human.

8. The system of claim 6, wherein the subject data comprises data corresponding to an activity level of the subject.

9. The system of claim 6, further comprising:
    means for defining the model and means for predicting the thermal strain; and
    means for simultaneously solving equations for conservation of energy and conservation of mass based on the received data.

10. The system of claim 6, further comprising means for calculating a radiant heat exchange rate among the fabric layers independent of the gap.

11. The system of claim 6, further comprising means for accounting for air exchange between the gap and ambient air external to the garments.

12. A method for modeling thermal comfort, said method comprising:
    defining a computerized model of a plurality of fabric layers on a subject to indicate thermal strain on the subject, said fabric layers having at least one gap therebetween;
    identifying input parameters for the defined model, wherein the input parameters include environmental condition data;
    receiving, from a user, a selection of a work environment from a plurality of predefined work environments;
    providing the defined model with the identified input parameters to a user, wherein executing the model produces output parameter data based on data corresponding to the input parameters and the selected work environment, said output parameter data providing an index of the thermal strain on the subject.

13. The method of claim 12, further comprising:
defining data corresponding to the subject, the fabric layers, and the gap; and
providing the defined data to the user for use with the provided model.

14. The method of claim 12, wherein defining the computerized model to indicate the thermal strain comprises defining the computerized model to predict a core temperature of the subject and a hydration level of the subject.

15. The method of claim 12, wherein providing the defined model to the user comprises providing the defined model to the user to enable the user to compare different combinations of fabric layers on the subject for product development.

16. The method of claim 12, wherein the input parameters describe a work situation, and wherein providing the defined model to the user comprises providing the defined model to the user to enable the user to identify differences in fabric performance in conditions represented by the input data, and to market the fabric layers based on the identified differences.

17. The method of claim 12, wherein providing the defined model to the user comprises providing the defined model to the user to enable the user to determine work-rest cycles for the subject based on the provided index of thermal strain.

18. The method of claim 12, wherein defining the computerized model comprises defining the computerized model to provide information related to skin health of the subject.

19. The method of claim 18, wherein the skin health comprises one or more of the following: skin hydration level, permeability of the skin to polar materials, and permeability of the skin to non-polar materials.

* * * * *

UNITED STATES PATENT AND TRADEMARK OFFICE
CERTIFICATE OF CORRECTION

PATENT NO.        : 8,005,655 B2                           Page 1 of 1
APPLICATION NO.   : 12/037825
DATED             : August 23, 2011
INVENTOR(S)       : Andrew Thomas Baker et al.

It is certified that error appears in the above-identified patent and that said Letters Patent is hereby corrected as shown below:

In the Specification

In Column 10, Line 22, delete "disp1ay" and insert -- display -- therefor.

In Column 10, Line 46, delete "disp1ay" and insert -- display -- therefor.

In TABLE 1, Column 13, Line 11, delete "6.46" and insert -- 6.46% -- therefor.

In Column 17, Line 6, delete "<Temp_Core>" and insert -- </Temp_Core> -- therefor.

Signed and Sealed this
Second Day of June, 2015

Michelle K. Lee
*Director of the United States Patent and Trademark Office*